(12) United States Patent
Guillemont et al.

(10) Patent No.: US 9,006,243 B2
(45) Date of Patent: Apr. 14, 2015

(54) HIV INHIBITING 6-SUBSTITUTED PYRIMIDINES

(75) Inventors: Jerôme Emile Georges Guillemont, Andé (FR); Céline Isabelle Mordant, Toulouse (FR)

(73) Assignee: Janssen R&D Ireland, Little Island, County Cork (IE)

( * ) Notice: Subject to any disclaimer, the term of this patent is extended or adjusted under 35 U.S.C. 154(b) by 1060 days.

(21) Appl. No.: 12/521,189

(22) PCT Filed: Dec. 28, 2007

(86) PCT No.: PCT/EP2007/064605
§ 371 (c)(1),
(2), (4) Date: Jun. 25, 2009

(87) PCT Pub. No.: WO2008/080964
PCT Pub. Date: Jul. 10, 2008

(65) Prior Publication Data
US 2010/0016317 A1    Jan. 21, 2010

(30) Foreign Application Priority Data
Dec. 29, 2006 (EP) ..................................... 06127325

(51) Int. Cl.
| | | |
|---|---|---|
| *C07D 239/48* | (2006.01) | |
| *A61K 31/506* | (2006.01) | |
| *C07D 401/04* | (2006.01) | |
| *C07D 401/12* | (2006.01) | |
| *C07D 403/06* | (2006.01) | |
| *C07D 405/12* | (2006.01) | |
| *C07D 409/12* | (2006.01) | |
| *C07D 417/06* | (2006.01) | |

(52) U.S. Cl.
CPC ............ *C07D 239/48* (2013.01); *C07D 401/04* (2013.01); *C07D 401/12* (2013.01); *C07D 403/06* (2013.01); *C07D 405/12* (2013.01); *C07D 409/12* (2013.01); *C07D 417/06* (2013.01)

(58) Field of Classification Search
USPC .......................... 544/122, 243, 295, 323, 324; 514/235.8, 252.14, 275
See application file for complete search history.

(56) References Cited

U.S. PATENT DOCUMENTS 3,459,731 A    8/1969 Gramera et al.
6,593,326 B1   7/2003 Bradbury et al.
(Continued)

FOREIGN PATENT DOCUMENTS

EP    0834507 B2    4/1998
WO   WO-97/18839 A1   5/1997
(Continued)

OTHER PUBLICATIONS

In the United States Patent and Trademark Office, Final-Office Action in re: U.S. Appl. No. 11/575,818, dated Feb. 2, 2011, 6 pages.
In the United States Patent and Trademark Office, Final-Office Action in re: U.S. Appl. No. 11/576,315, dated Feb. 2, 2011, 6 pages.
In the United States Patent and Trademark Office, Final-Office Action in re: U.S. Appl. No. 12/294,692, dated May 13, 2011, 10 pages.
In the United States Patent and Trademark Office, Non-Final-Office Action in re: U.S. Appl. No. 11/575,818, dated Aug. 5, 2010, 7 pages.
In the United States Patent and Trademark Office, Non-Final-Office Action in re: U.S. Appl. No. 11/576,315, dated Aug. 5, 2010, 7 pages.
(Continued)

*Primary Examiner* — Deepak Rao
(74) *Attorney, Agent, or Firm* — Bernard F. Plantz; Johnson & Johnson

(57) ABSTRACT

HIV replication inhibitors of formula

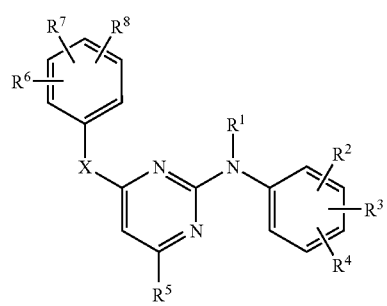

$R^1$ is hydrogen; aryl; formyl; $C_{1-6}$alkylcarbonyl; $C_{1-6}$alkyl; $C_{1-6}$alkyloxycarbonyl;
$R^2$, $R^3$, $R^6$ and $R^7$ are hydrogen; hydroxy; halo; $C_{3-7}$cycloalkyl; $C_{1-6}$alkyloxy; carboxyl; $C_{1-6}$alkyloxycarbonyl; cyano; nitro; amino; mono- or di($C_{1-6}$alkyl)amino; polyhalo$C_{1-6}$alkyl; polyhalo$C_{1-6}$alkyloxy; —C(=O)$R^9$; optionally substituted $C_{1-6}$alkyl, $C_{2-6}$alkenyl or $C_{2-6}$alkynyl;
$R^4$ and $R^5$ are hydroxy; halo; $C_{3-7}$cycloalkyl; $C_{1-6}$alkyloxy; carboxyl; $C_{1-6}$alkyloxycarbonyl; formyl; cyano; nitro; amino; mono- or di($C_{1-6}$alkyl)amino; polyhalo$C_{1-6}$alkyl; polyhalo$C_{1-6}$alkyloxy; —C(=O)$R^9$; cyano; —S(=O)$_r R^9$; —NH—S(=O)$_2 R^9$; —NHC(=O)H; —C(=O)NHNH$_2$; —NHC(=O)$R^9$; Het; —Y-Het; optionally substituted $C_{1-6}$alkyl, $C_{2-6}$alkenyl or $C_{2-6}$alkynyl;
$R^5$ is pyridyl; —C(=O)N$R^{5a}R^{5b}$; —CH(O$R^{5c}$)$R^{5d}$; —CH$_2$—N$R^{5e}R^{5f}$; —CH=NO$R^{5a}$; —CH$_2$—O—C$_{2-6}$alkenyl; —CH$_2$—O—P(=O)(O$R^{5g}$)$_2$; —CH$_2$—O—C(=O)—NH$_2$; —C(=O)—$R^{5d}$;
X is —N$R^1$—, —O—, —CH$_2$—, —S—;
pharmaceutical compositions containing these compounds as active ingredient and processes for preparing said compounds and compositions.

14 Claims, No Drawings

(56) References Cited

U.S. PATENT DOCUMENTS

| | | |
|---|---|---|
| 7,504,396 B2 | 3/2009 | Nunes et al. |
| 7,531,548 B2 * | 5/2009 | Guillemont et al. .......... 514/272 |
| 8,163,745 B2 * | 4/2012 | Guillemont et al. ....... 514/235.8 |
| 2003/0036543 A1 | 2/2003 | Bebbington |
| 2005/0209221 A1 | 9/2005 | Nunes et al. |
| 2008/0262007 A1 | 10/2008 | Guillemont et al. |
| 2009/0181993 A1 | 7/2009 | Guillemont et al. |
| 2010/0168104 A1 | 7/2010 | Guillemont et al. |
| 2010/0261722 A1 | 10/2010 | Guillemont et al. |

FOREIGN PATENT DOCUMENTS

| | | |
|---|---|---|
| WO | WO-99/50250 A1 | 10/1999 |
| WO | WO-99/50256 A1 | 10/1999 |
| WO | WO-00/27825 A1 | 5/2000 |
| WO | WO-00/39101 A1 | 7/2000 |
| WO | WO 0185700 A | 11/2001 |
| WO | WO-03/016306 A1 | 2/2003 |
| WO | WO-03/063794 A2 | 8/2003 |
| WO | WO-2004/046143 A1 | 6/2004 |
| WO | WO-2005/009443 A1 | 2/2005 |
| WO | WO-2006/035067 A2 | 4/2006 |
| WO | WO 2006/035069 A | 4/2006 |
| WO | WO-2007/113254 A1 | 10/2007 |
| WO | WO-2008/080965 A1 | 7/2008 |

OTHER PUBLICATIONS

In the United States Patent and Trademark Office, Non-Final-Office Action in re: U.S. Appl. No. 12/294,692, dated Nov. 26, 2010, 8 pages.

In the United States Patent and Trademark Office, Non-Final-Office Action in re: U.S. Appl. No. 12/521,379, dated Sep. 26, 2011, 8 pages.

International Search Report from PCT/EP2005/054930, dated Jun. 20, 2006.

International Search Report from PCT/EP2005/054932, dated Sep. 12, 2005.

International Search Report from PCT/EP2007/053111, dated Aug. 14, 2007.

International Search Report from PCT/EP2007/064605, dated May 6, 2008.

International Search Report from PCT/EP2007/064606, dated Jul. 14, 2008.

Ludovici, D. et al., "Evolution of Anti-HIV Drug Candidates. Part 3: Diarylpyrimidine (DAPY) Analogues"; *Bioorganic & Medicinal Chemistry Letters*, 2001; 11:2235-2239.

Nogradi, N, "Dimethyl-p-Cyclodextrin," *Drugs of the Future*, 9(8):577-578, 1984.

Vippagunta, S. et al., "Crystalline solids,"*Advanced Drug Delivery Reviews*, 2001; 48: 3-26.

* cited by examiner

HIV INHIBITING 6-SUBSTITUTED PYRIMIDINES

This invention concerns pyrimidine derivatives having HIV (Human Immunodeficiency Virus) replication inhibiting properties, the preparation thereof and pharmaceutical compositions comprising these compounds.

Initially, treatment of HIV infection consisted of monotherapy with nucleoside derivatives and although successful in suppressing viral replication, these drugs quickly lost their effectiveness due to the emergence of drug-resistant strains. It became clear that a high mutation rate combined with rapid replication made HIV a particularly challenging target for antiviral therapy. The introduction of combination therapy of two or more anti-HIV agents improved therapeutic outcome. Significant progress was made by the introduction of HAART (Highly Active Anti-Retroviral Therapy) that resulted in a powerful and sustained virus suppression. HAART typically involves combinations of nucleoside or nucleotide reverse transcriptase inhibitors (NRTIs or NtRTIs respectively) with a non-nucleoside reverse transcriptase inhibitor (NNRTI) or a protease inhibitor (PI). Current guidelines for antiretroviral therapy recommend such triple combination therapy regimen even for initial treatment. These multidrug therapies however do not completely eliminate HIV and long-term treatment usually results in multidrug resistance. It also has been shown that resistant virus is carried over to newly infected individuals, resulting in severely limited therapy options for these drug-naive patients.

Therefore there is a continued need for new combinations of active ingredients that are effective against HIV. New types of anti-HIV effective active ingredients, differing in chemical structure and activity profile are useful in new types of combination therapy. Finding such active ingredients therefore is a highly desirable goal to achieve.

The present invention is aimed at providing particular novel series of pyrimidine derivatives having HIV replication inhibiting properties. WO 99/50250, WO 00/27825, WO 01/85700, and WO 06/035067 disclose certain classes of substituted aminopyrimidines having HIV replication inhibiting properties.

The compounds of the invention differ from prior art compounds in structure, pharmacological activity and/or pharmacological potency. It has been found that the introduction of certain substituents in the 6-position of the pyrimidine moiety results in compounds not only acting favorably in terms of their capability to inhibit the replication of Human Immunodeficiency Virus (HIV), but also by their improved ability to inhibit the replication of mutant strains, in particular of strains that show resistance to known NNRTI drugs, which strains are referred to as drug- or multidrug-resistant HIV strains.

Thus in one aspect, the present invention concerns compounds of formula

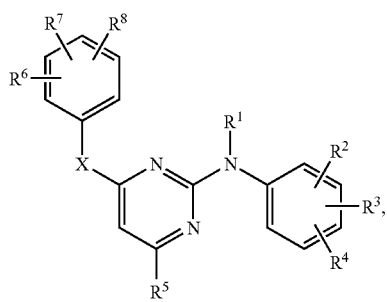

(I)

the pharmaceutically acceptable addition salts, the pharmaceutically acceptable solvates, and stereochemically isomeric forms thereof, wherein:

each $R^1$ independently is hydrogen; aryl; formyl; $C_{1-6}$alkylcarbonyl; $C_{1-6}$alkyl; $C_{1-6}$alkyloxycarbonyl;

$R^2$, $R^3$, $R^6$ and $R^7$ independently are hydrogen; hydroxy; halo; $C_{3-7}$cycloalkyl; $C_{1-6}$alkyloxy; carboxyl; $C_{1-6}$alkyloxycarbonyl; cyano; nitro; amino; mono- or di($C_{1-6}$alkyl)amino; polyhalo$C_{1-6}$alkyl; polyhalo$C_{1-6}$alkyloxy; —C(=O)$R^9$; $C_{1-6}$alkyl optionally substituted with halo, cyano or —C(=O)$R^9$; $C_{2-6}$alkenyl optionally substituted with halo, cyano or —C(=O)$R^9$; $C_{2-6}$alkynyl optionally substituted with halo, cyano or —C(=O)$R^9$;

$R^4$ and $R^8$ independently are hydroxy; halo; $C_{3-7}$cycloalkyl; $C_{1-6}$alkyloxy; carboxyl; $C_{1-6}$alkyloxycarbonyl; formyl; cyano; nitro; amino; mono- or di($C_{1-6}$alkyl)amino; polyhalo$C_{1-6}$alkyl; polyhalo$C_{1-6}$alkyloxy; —C(=O)$R^9$; —S(=O)$R^9$; —NH—S(=O)$_2R^9$; —NHC(=O)H; —C(=O)NHNH$_2$; —NHC(=O)$R^9$; Het; —Y-Het; $C_{1-6}$alkyl optionally substituted with halo, cyano, amino, mono- or di($C_{1-6}$alkyl)amino, —C(=O)—$R^9$, Het or with $C_{1-6}$alkyloxy; $C_{2-6}$alkenyl optionally substituted with halo, cyano, amino, mono- or di($C_{1-6}$alkyl)amino, —C(=O)—$R^9$, Het, or with $C_{1-6}$alkyloxy; $C_{2-6}$alkynyl optionally substituted with halo, cyano, amino, mono- or di($C_{1-6}$alkyl)amino, —C(=O)—$R^9$, Het, or with $C_{1-6}$alkyloxy;

$R^5$ is pyridyl; —C(=O)NR$^{5a}$R$^{5b}$; —CH(OR$^{5c}$)R$^{5d}$; —CH$_2$—NR$^{5e}$R$^{5f}$; —CH=NOR$^{5a}$; —CH$_2$—O—C$_{2-6}$alkenyl; —CH$_2$—O—P(=O)(OR$^{5g}$)$_2$; —CH$_2$—O—C(=O)—NH$_2$; —C(=O)—R$^{5d}$;

each $R^{5a}$ independently is hydrogen or $C_{1-6}$alkyl;

$R^{5b}$ is $C_{1-6}$alkyloxy; or $C_{1-6}$alkyl substituted with hydroxy, $C_{1-6}$alkyloxy, halo, cyano, Het;

$R^{5c}$ is hydrogen, $C_{1-6}$alkyl, Het;

each $R^{5d}$ independently is aryl or Het;

$R^{5e}$ is hydrogen or $C_{1-6}$alkyl;

$R^{5f}$ is $C_{1-6}$alkyloxy; $C_{2-6}$alkenyl; or $C_{1-6}$alkyl substituted with a radical selected from hydroxy, $C_{1-6}$alkyloxy, cyano, amino, mono- and di-$C_{1-6}$alkylamino, $C_{1-6}$alkylcarbonylamino, aryl, Het, dioxolanyl, tetrahydrofuranyl, pyrrolidinyl, piperidinyl, morpholinyl, piperazinyl, piperazinyl, and $C_{3-7}$cycloalkyl; wherein said dioxolanyl may be optionally substituted with one or two $C_{1-6}$alkyl radicals; and wherein said piperazinyl may be optionally substituted with $C_{1-6}$alkyl, $C_{1-6}$alkylcarbonyl, or with $C_{1-6}$alkyloxycarbonyl;

$R^{5e}$ and $R^{5f}$ taken together with the nitrogen atom on which they are substituted form pyrrolidinyl; imidazolyl; piperidinyl; morpholinyl; piperazinyl; or piperazinyl optionally substituted with $C_{1-6}$alkyl, $C_{1-6}$alkyloxycarbonyl, or with $C_{1-6}$alkylcarbonyl;

each $R^{5g}$ independently is $C_{1-6}$alkyl;

each $R^9$ independently is $C_{1-6}$alkyl, amino, mono- or di($C_{1-6}$alkyl)amino, or polyhalo-$C_{1-6}$alkyl;

X is —NR$^1$—, —O—, —CH$_2$—, —S—;

each r independently is 1 or 2;

each Het independently is pyridyl, thienyl, furanyl, oxazolyl, isoxazolyl, imidazolyl, pyrazolyl, thiazolyl, thiadiazolyl, oxadiazolyl, quinolinyl, benzothienyl, benzofuranyl; which each may optionally be substituted with one or two substituents each independently selected from $C_{1-6}$alkyl, halo, hydroxy, cyano, $C_{1-6}$alkyloxy, $C_{2-6}$alkenyl substituted with halo, hydroxy or with cyano;

each aryl independently is phenyl or phenyl substituted with one, two, three, four or five substituents each independently selected from halo, hydroxy, mercapto, $C_{1-6}$alkyl, $C_{2-6}$alkenyl, $C_{2-6}$alkynyl, hydroxy$C_{1-6}$alkyl, aminoC$_{1-6}$alkyl, mono or di(C$_{1-6}$alkyl)aminoC$_{1-6}$alkyl, C$_{1-6}$alkylcarbonyl, C$_{3-7}$cycloalkyl, C$_{1-6}$alkyloxy, phenylC$_{1-6}$alkyloxy, C$_{1-6}$alkyloxycarbonyl, aminosulfonyl, C$_{1-6}$alkylthio, cyano, nitro, polyhaloC$_{1-6}$alkyl, polyhaloC$_{1-6}$alkyloxy, aminocarbonyl, phenyl, Het and —Y-Het.

As used hereinbefore or hereinafter C$_{1-4}$alkyl as a group or part of a group defines straight or branched chain saturated hydrocarbon radicals having from 1 to 4 carbon atoms such as methyl, ethyl, 1-propyl, 2-propyl, 1-butyl, 2-butyl, 2-methylpropyl, t.butyl; C$_{1-6}$alkyl as a group or part of a group defines straight or branched chain saturated hydrocarbon radicals having from 1 to 6 carbon atoms such as the group defined for C$_{1-4}$alkyl and 1-pentyl, 2-pentyl, 1-hexyl, 2-hexyl, 3-hexyl, 2-methylbutyl, 3-methylpentyl, and the like; C$_{1-2}$alkyl defines methyl or ethyl; C$_{3-7}$cycloalkyl is generic to cyclopropyl, cyclobutyl, cyclopentyl, cyclohexyl and cycloheptyl. Preferred amongst C$_{1-6}$alkyl are C$_{1-4}$alkyl or C$_{1-2}$alkyl. Preferred amongst C$_{3-7}$cycloalkyl are cyclopentyl or cyclohexyl.

The term "C$_{2-6}$alkenyl" as a group or part of a group defines straight and branched chained hydrocarbon radicals having saturated carbon-carbon bonds and at least one double bond, and having from 2 to 6 carbon atoms, such as, for example, ethenyl (or vinyl), 1-propenyl, 2-propenyl (or allyl), 1-butenyl, 2-butenyl, 3-butenyl, 2-methyl-2-propenyl, 1-pentenyl, 2-pentenyl, 3-pentenyl, 2-methyl-1-butenyl, 1-hexenyl, 2-hexenyl, 3-hexenyl, 4-hexenyl, 2-methyl-2-pentenyl, 1,2-dimethyl-1-butenyl and the like. Preferred are C$_{2-6}$alkenyls having one double bond. Of interest amongst C$_{2-6}$alkenyl radicals are the C$_{2-4}$alkenyl radicals. The term "C$_{3-6}$alkenyl" is as C$_{2-6}$alkenyl but is limited to unsaturated hydrocarbon radicals having from 3 to 6 carbon atoms. In the instances where a C$_{3-6}$alkenyl is linked to a heteroatom, the carbon atom linked to the heteroatom by preference is saturated.

The term "C$_{2-6}$alkynyl" as a group or part of a group defines straight and branched chained hydrocarbon radicals having saturated carbon-carbon bonds and at least one triple bond, and having from 2 to 6 carbon atoms, such as, for example, ethynyl, 1-propynyl, 2-propynyl, 1-butynyl, 2-butynyl, 3-butynyl, 2-methyl-2-propynyl, 2-pentynyl, 3-pentynyl, 2-hexynyl, 3-hexynyl, 4-hexynyl, 2-methyl-2-butynyl, 2-methyl-2-pentynyl and the like. Preferred are C$_{2-6}$alkynyls having one triple bond. Of interest amongst C$_{2-6}$alkynyl radicals are the C$_{2-4}$alkynyl radicals. The term "C$_{3-6}$alkynyl" is as C$_{2-6}$alkynyl but is limited to unsaturated hydrocarbon radicals having from 3 to 6 carbon atoms. In the instances where a C$_{3-6}$alkynyl is linked to a heteroatom, the carbon atom linked to the heteroatom by preference is saturated.

As used herein before, the term (=O) refers to a carbonyl moiety when attached to a carbon atom, a sulfoxide moiety when attached to a sulfur atom and a sulfonyl moiety when two of said terms are attached to a sulfur atom.

The terms carboxyl, carboxy or hydroxycarbonyl refer to a group —COOH.

The term "halo" is generic to fluoro, chloro, bromo or iodo.

The term "polyhaloC$_{1-6}$alkyl" as a group or part of a group, e.g. in polyhaloC$_{1-6}$alkoxy, is defined as mono- or polyhalo substituted C$_{1-6}$alkyl, in particular C$_{1-6}$alkyl substituted with up to one, two, three, four, five, six, or more halo atoms, such as methyl or ethyl with one or more fluoro atoms, for example, difluoromethyl, trifluoromethyl, trifluoro-ethyl. Preferred is trifluoromethyl. Also included are perfluoroC$_{1-6}$alkyl groups, which are C$_{1-6}$alkyl groups wherein all hydrogen atoms are replaced by fluoro atoms, e.g. pentafluoroethyl. In case more than one halogen atom is attached to an alkyl group within the definition of polyhaloC$_{1-6}$alkyl, the halogen atoms may be the same or different.

Any of the heterocycles mentioned in the definitions of Het may comprise any isomer such as for example oxadiazole may be 1,2,4-oxadiazole, 1,3,4-oxadiazole, or 1,2,3-oxadiazole; likewise for the group thiadiazole, which may be 1,2,4-thiadiazole, 1,3,4-thiadiazole, or 1,2,3-thiadiazole; similarly, pyrrole may be 1H-pyrrole, or 2H-pyrrole. The group Het can be oxazolyl or thiazoyl, which preferably are 1,3-oxazolyl or 1,3-thiazolyl, respectively.

Any pyrrolidinyl, piperidinyl, morpholinyl, piperazinyl, piperazinyl in particular is substituted to the remainder of the molecule via its nitrogen atom. Any piperazinyl being substituted such as with C$_{1-6}$alkyl, C$_{1-6}$alkylcarbonyl, or with hydroxyC$_{1-6}$alkyl, is preferably substituted at the nitrogen through which the piperazine is not connected to the remainder of the molecule (in many instances the 4-nitrogen).

In one embodiment each Het independently is pyridyl, thienyl, furanyl, oxazolyl, or thiazolyl.

Whenever a radical occurs in the definition of the compounds of formula (I) or in any of the subgroups specified herein, said radical independently is as specified above in the definition of the compounds of formulas (I) or in the more restricted definitions as specified hereinafter.

It should also be noted that the radical positions on any molecular moiety used in the definitions may be anywhere on such moiety as long as it is chemically stable. For instance pyridine includes 2-pyridine, 3-pyridine and 4-pyridine; pentyl includes 1-pentyl, 2-pentyl and 3-pentyl.

When any variable (e.g. halogen, C$_{1-6}$alkyl, aryl, Het, etc.) occurs more than one time in any moiety, each definition is independent. Any limited definitions of the radicals specified herein are meant to be applicable to the group of compounds of formula (I) as well as to any subgroup defined or mentioned herein. Lines drawn from substituents into ring systems indicate that the bond may be attached to any of the suitable ring atoms.

The pharmaceutically acceptable addition salt forms, which the compounds of the present invention are able to form, can conveniently be prepared using the appropriate acids, such as, for example, inorganic acids such as hydrohalic acids, e.g. hydrochloric or hydrobromic acid, sulfuric, hemisulphuric, nitric, phosphoric and the like acids; or organic acids such as, for example, acetic, aspartic, dodecylsulphuric, heptanoic, hexanoic, nicotinic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-amino-salicylic, pamoic and the like acids. Conversely said acid addition salt forms can be converted into the free base form by treatment with an appropriate base.

The compounds of formula (I) containing acidic protons may be converted into their pharmaceutically acceptable metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, the benzathine, N-methyl-D-glucamine, 2-amino-2-(hydroxymethyl)-1,3-propanediol, hydrabamine salts, and salts with amino acids such as, for example, arginine, lysine and the like. Conversely the salt form can be converted by treatment with acid into the free acid form.

The term "pharmaceutically acceptable solvate" is meant to comprise hydrates and solvent addition forms that the compounds of formula (I), including stereoisomeric forms thereof, can form. Examples of such solvates are e.g. hydrates, alcoholates, such as methanolates, ethanolates, i.propanolates, n.propanolates, and the like.

The compounds of formula (I) thereof may contain one or more centers of chirality and may exist as stereochemically isomeric forms. Of special interest are those compounds of formula (I) that are stereochemically pure. The term "stereochemically isomeric forms" as used herein defines all the possible stereoisomeric forms, which the compounds of formula (I) and the addition salts thereof may possess. Unless otherwise mentioned or indicated, the chemical designation of compounds denotes the mixture of all possible stereochemically isomeric forms, said mixtures containing all diastereomers and enantiomers of the basic molecular structure as well as each of the individual isomeric forms of formula (I) the pharmaceutically acceptable salts or the pharmaceutically acceptable solvates substantially free, i.e. associated with less than 10%, preferably less than 5%, in particular less than 2% and most preferably less than 1% of the other isomers. Thus, when a compound of formula (I) is for instance specified as (E), this means that the compound is substantially free of the (Z) isomer. In particular, stereogenic centers may have the R- or S-configuration; substituents on bivalent cyclic (partially) saturated radicals may have either the cis- or trans-configuration.

Compounds having double bonds can have an E (entgegen) or Z (zusammen)-stereochemistry at said double bond. The terms cis, trans, R, S, E and Z are well known to a person skilled in the art.

Some of the compounds of formula (I) may also exist in their tautomeric form. Such forms although not explicitly indicated in the above formula are intended to be included within the scope of the present invention.

The present invention is also intended to include any isotopes of atoms present in the compounds of the invention. For example, isotopes of hydrogen include tritium and deuterium and isotopes of carbon include C-13 and C-14.

Whenever used hereinabove or hereinafter, the terms "compounds of formula (I)", "the present compounds", "the compounds of the present invention" or any equivalent terms, and similarly, the terms "subgroups of compounds of formula (I)", "subgroups of the present compounds", "subgroups of the compounds of the present invention" or any equivalent terms, are meant to include the compounds of general formula (I), or subgroups of the compounds of general formula (I), as well as their salts, solvates, and stereoisomers.

Whenever mention is made hereinbefore or hereinafter that substituents can be selected each independently out of a list of definitions, such as for example for $R^1$ and $R^{5d}$, any possible combinations are intended to be included, which are chemically possible or which lead to molecules of such chemical stability that they can be processed in standard pharmaceutical procedures.

One embodiment of the present invention concerns compounds of formula

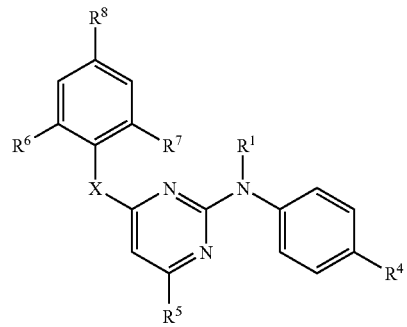

(I-a)

the pharmaceutically acceptable addition salts or stereochemically isomeric forms thereof, wherein X, $R^1$, $R^4$, $R^5$, $R^6$, $R^7$, and $R^8$ are as defined above or hereinafter.

In one embodiment, $R^8$ in the compounds of formula (I) or (I-a) is $C_{1-6}$alkyl, $C_{2-6}$alkenyl, or $C_{1-6}$alkynyl each substituted with cyano. In another embodiment, $R^8$ in the compounds of formula (I) or (I-a) is $C_2$alkyl, $C_2$alkenyl, or $C_2$alkynyl, each substituted with cyano; wherein the cyano in particular is substituted at a carbon atom that is not linked to the phenyl group. In the latter instance, $R^8$ can be represented by a radical -A-CN, wherein A is —$CH_2$—$CH_2$—, —CH=CH—, or —C≡C—.

Particular subgroups of the compounds of formula (I) or (I-a) or any subgroup of compounds of formula (I) or (I-a) specified herein wherein
(a) $R^8$ is —$CH_2$—$CH_2$—CN or —CH=CH—CN; or wherein (b) $R^8$ is —CH=CH—CN.

Of particular interest are those compounds of formula (I) as defined herein, or of any of the subgroups thereof, wherein $R^8$ is —CH=CH—, substituted with any of the $C_{2-6}$alkenyl substituents specified above in relation to the definition of $R^8$, or wherein $R^8$ in particular is —CH=CH—CN, and wherein the substituents on the —CH=CH— moiety are in an E-configuration (i.e. the so-called 'E'-isomers). Of special interest are those compounds of formula (I) as defined herein, or of any of the subgroups thereof, wherein $R^8$ is (E) —CH=CH—CN.

Embodiments of the present invention are those compounds of formula (I) or any of the subgroups of compounds of formula (I) wherein $R^1$ is hydrogen.

Further embodiments of the present invention are those compounds of formula (I) or any of the subgroups of compounds of formula (I) wherein
(a) $R^2$, $R^3$, $R^6$ and $R^7$ independently are hydrogen; hydroxy; halo; $C_{1-6}$alkyl; $C_{3-7}$cyclo-alkyl; $C_{1-6}$alkyloxy; carboxyl; $C_{1-6}$alkyloxycarbonyl; cyano; nitro; amino; mono- or di($C_{1-6}$alkyl)amino; polyhalo$C_{1-6}$alkyl; polyhalo$C_{1-6}$alkyloxy; —C(=O)$R^9$; or
(b) $R^2$, $R^3$, $R^6$ and $R^7$ independently are hydrogen; hydroxy; halo; $C_{1-6}$alkyl; $C_{1-6}$alkyloxy; carboxyl; $C_{1-6}$alkyloxycarbonyl; cyano; nitro; amino; mono- or di($C_{1-6}$alkyl)amino; polyhalo$C_{1-6}$alkyl; —C(=O)$R^9$; or
(c) $R^2$, $R^3$, $R^6$ and $R^7$ independently are hydrogen; hydroxy; halo; $C_{1-6}$alkyl; or $C_{1-6}$alkyloxy; cyano; amino; mono- or di($C_{1-6}$alkyl)amino; polyhalo$C_{1-6}$alkyl;
(d) $R^2$, $R^3$, $R^6$ and $R^7$ independently are hydrogen; halo; $C_{1-6}$alkyl; cyano; or (e) R² and R³ are hydrogen and R⁶ and R⁷ independently are hydrogen; halo; cyano.

Embodiments of the present invention are those compounds of formula (I) or any of the subgroups of compounds of formula (I) wherein
(a) R⁴ and R⁸ independently are halo; carboxyl; $C_{1-6}$alkyloxycarbonyl; cyano; —C(=O)R⁹; Het; —Y-Het; $C_{1-6}$alkyl optionally substituted with cyano, —C(=O)—R⁹, Het; $C_{2-6}$alkenyl optionally substituted with cyano, —C(=O)—R⁹, Het; and wherein each Het in particular is independently selected from thienyl, furanyl, oxazolyl, thiazolyl, which each may be optionally substituted with halo, $C_{1-6}$alkyl, cyano; or
(b) R⁴ and R⁸ independently are cyano; —C(=O)R⁹; Het; $C_{1-6}$alkyl optionally substituted with cyano, —C(=O)—R⁹, Het; $C_{2-6}$alkenyl optionally substituted with cyano, —C(=O)—R⁹, Het; and wherein each Het in particular is independently thienyl or furanyl, each optionally substituted with cyano; or
(c) R⁴ and R⁸ independently are cyano; $C_{1-6}$alkyl substituted with cyano; $C_{2-6}$alkenyl substituted with cyano; or
(d) R⁴ is cyano; R⁸ is $C_{2-6}$alkenyl substituted with cyano.

Embodiments of the present invention are those compounds of formula (I) or any of the subgroups of compounds of formula (I) wherein
R⁵ is pyridyl; or R⁵ is
—CONR$^{5a}$R$^{5b}$; wherein R$^{5a}$ independently is hydrogen or $C_{1-6}$alkyl;
R$^{5b}$ is $C_{1-6}$alkyloxy; or $C_{1-6}$alkyl substituted with $C_{1-6}$alkyloxy, halo, cyano, pyridyl, thienyl, furanyl, thiazolyl, or with oxazolyl; or R$^{5b}$ is $C_{1-6}$alkyloxy; or $C_{1-6}$alkyl substituted with $C_{1-6}$alkyloxy, halo, cyano, pyridyl, or with furanyl;
—CH(OR$^{5c}$)R$^{5d}$; wherein R$^{5c}$ is hydrogen and R$^{5d}$ is aryl;
—CH₂—NR$^{5e}$R$^{5f}$; R$^{5e}$ is hydrogen or $C_{1-6}$alkyl; wherein R$^{5f}$ is $C_{1-6}$alkyloxy; $C_{2-6}$alkenyl; or $C_{1-6}$alkyl substituted with hydroxy, $C_{1-6}$alkyloxy, cyano, amino, mono- or di-$C_{1-6}$alkylamino, $C_{1-6}$alkylcarbonylamino, aryl, pyridyl, thienyl, furanyl, tetrahydrofuranyl, morpholinyl, $C_{3-7}$cycloalkyl, or with dioxolanyl optionally substituted with two $C_{1-6}$alkyl radicals; or R$^{5e}$ and R$^{5f}$ taken together with the nitrogen atom on which they are substituted form imidazolyl; morpholinyl; piperazinyl; or piperazinyl optionally substituted with $C_{1-6}$alkyl;
—CH=NOR$^{5a}$; wherein R$^{5a}$ is $C_{1-6}$alkyl;
—CH₂—O—$C_{2-6}$alkenyl;
—CH₂—O—P(=O)(OR$^{5g}$)₂; wherein each R$^{5g}$ independently is $C_{1-6}$alkyl;
—CH₂—O—C(=O)—NH₂;
—C(=O)—R$^{5d}$; wherein R$^{5d}$ is pyridyl, thienyl, furanyl, thiazolyl, oxazolyl; or
wherein R$^{5d}$ is thiazolyl.

Embodiments of the present invention are those compounds of formula (I) or any of the subgroups of compounds of formula (I) wherein each R⁹ independently is $C_{1-6}$alkyl, amino, mono- or di($C_{1-6}$alkyl)amino.

Embodiments of the present invention are those compounds of formula (I) or any of the subgroups of compounds of formula (I) wherein
(a) X is —NR¹—, —O—; or
(b) X is —NR¹—; or
(c) X is —N($C_{1-6}$alkyl)-; or
(d) X is —NH—; or
(e) X is —NH— or —O—.

Embodiments of the present invention are those compounds of formula (I) or any of the subgroups of compounds of formula (I) wherein each r is 2.

Embodiments of the present invention are those compounds of formula (I) or any of the subgroups of compounds of formula (I) wherein
(a) each Het independently is pyridyl, thienyl, furanyl, oxazolyl, isoxazolyl, imidazolyl, pyrazolyl, thiazolyl, thiadiazolyl, oxadiazolyl, quinolinyl, benzothienyl, benzofuranyl; which each may optionally be substituted with one or two substituents each independently selected from $C_{1-6}$alkyl, halo, hydroxy, cyano, $C_{1-6}$alkyloxy, $C_{2-6}$alkenyl substituted with halo, hydroxy or with cyano; or
(b) each Het independently is pyridyl, thienyl, furanyl, oxazolyl, thiazolyl; which each may optionally be substituted with $C_{1-6}$alkyl, halo; or
(c) each Het independently is pyridyl, thienyl, furanyl, oxazolyl, thiazolyl; or
(d) each Het independently is pyridyl, thienyl, furanyl.

Embodiments of the present invention are those compounds of formula (I) or any of the subgroups of compounds of formula (I) wherein each aryl independently is phenyl or phenyl substituted with one, two or three substituents each independently selected from those mentioned above or in particular selected from:
(a) halo, hydroxy, $C_{1-6}$alkyl, $C_{2-6}$alkenyl, $C_{2-6}$alkynyl, hydroxy$C_{1-6}$alkyl, amino-$C_{1-6}$alkyl, mono or di($C_{1-6}$alkyl)amino$C_{1-6}$alkyl, $C_{1-6}$alkylcarbonyl, $C_{3-7}$cycloalkyl, $C_{1-6}$alkyloxy, phenyl$C_{1-6}$alkyloxy, $C_{1-6}$alkyloxycarbonyl, aminosulfonyl, cyano, nitro, polyhalo$C_{1-6}$alkyl, polyhalo$C_{1-6}$alkyloxy, aminocarbonyl, phenyl, Het or —Y-Het; or
(b) halo, hydroxy, $C_{1-6}$alkyl, hydroxy$C_{1-6}$alkyl, amino$C_{1-6}$alkyl, mono or di($C_{1-6}$alkyl)amino$C_{1-6}$alkyl, $C_{1-6}$alkyloxy, phenyl$C_{1-6}$alkyloxy, $C_{1-6}$alkyloxycarbonyl, cyano, polyhalo$C_{1-6}$alkyl, aminocarbonyl; or
(c) halo, hydroxy, $C_{1-6}$alkyl, hydroxy$C_{1-6}$alkyl, amino $C_{1-6}$alkyl, $C_{1-6}$alkyloxy, cyano, trifluoromethyl; or
(d) halo, hydroxy, $C_{1-6}$alkyl, $C_{1-6}$alkyloxy, cyano, trifluoromethyl.

Particular subgroups of compounds of formula (I) or (I-a) are those wherein one, several or all of the following limitations apply:
R¹ is hydrogen;
R⁴ is hydroxy, halo, $C_{1-6}$alkyl, carboxyl, cyano, —C(=O)R⁹, nitro, amino, mono- or di($C_{1-6}$alkyl)amino, polyhalomethyl;
X is —NR¹—, —O—, —S—;
R⁵ is pyridyl; or R⁵ is
—CONR$^{5a}$R$^{5b}$; wherein R$^{5a}$ independently is hydrogen or $C_{1-6}$alkyl;
R$^{5b}$ is $C_{1-6}$alkyloxy; or $C_{1-6}$alkyl substituted with $C_{1-6}$alkyloxy, halo, cyano, pyridyl, furanyl;
—CH(OR$^{5c}$)R$^{5d}$; wherein R$^{5c}$ is hydrogen and R$^{5d}$ is aryl;
—CH₂—NR$^{5e}$R$^{5f}$; R$^{5e}$ is hydrogen or $C_{1-6}$alkyl;
R$^{5f}$ is $C_{1-6}$alkyloxy; $C_{2-6}$alkenyl; or $C_{1-6}$alkyl substituted with hydroxy, $C_{1-6}$alkyloxy, cyano, amino, mono- or di-$C_{1-6}$alkylamino, $C_{1-6}$alkyl-carbonylamino, aryl, pyridyl, thienyl, furanyl, dioxolanyl optionally substituted with two $C_{1-6}$alkyl radicals, tetrahydrofuranyl, morpholinyl, $C_{3-7}$cycloalkyl; or
R$^{5e}$ and R$^{5f}$ taken together with the nitrogen atom on which they are substituted form imidazolyl; morpholinyl; piperazinyl; or piperazinyl optionally substituted with $C_{1-6}$alkyl;
—CH=NOR$^{5a}$; wherein R$^{5a}$ is $C_{1-6}$alkyl;
—CH₂—O—$C_{2-6}$alkenyl;
—CH₂—O—P(=O)(OR$^{5g}$)₂; each R$^{5g}$ independently is $C_{1-6}$alkyl;
—CH₂—O—C(=O)—NH₂;
—C(=O)—R$^{5d}$; wherein R$^{5d}$ thiazolyl;

each aryl independently is phenyl or phenyl substituted with one, two, or three substituents each independently selected from halo, hydroxy, $C_{1-6}$alkyl, hydroxy-$C_{1-6}$alkyl, amino$C_{1-6}$alkyl, mono or di($C_{1-6}$alkyl)amino$C_{1-6}$alkyl, $C_{1-6}$alkyl-carbonyl, $C_{3-7}$cycloalkyl, $C_{1-6}$alkyloxy, $C_{1-6}$alkyloxycarbonyl, $C_{1-6}$alkylthio, cyano, nitro, trifluoromethyl, aminocarbonyl.

The compounds of formula (I) can be prepared by reacting an intermediate of formula (II), wherein W represents a suitable leaving group, such as for example halogen, e.g. chloro, bromo, or a tosyl, mesyl, or similar group, with an intermediate of formula (III).

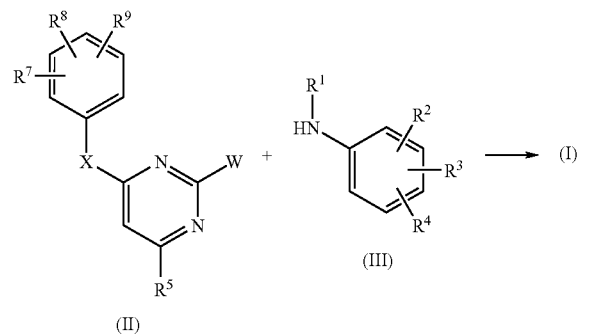

The reaction of (II) with (III) is usually conducted in the presence of a suitable solvent. Suitable solvents are for example an alcohol, such as for example ethanol, 2-propanol; a dipolar aprotic solvent such as acetonitrile, N,N-dimethylformamide, N,N-dimethyl-acetamide, 1-methyl-2-pyrrolidinone; an ether such as tetrahydrofuran, 1,4-dioxane, propylene glycol monomethylether. The reaction can be done under acid conditions obtained by adding amounts of a suitable acid such as for example camphor sulfonic acid, or by using acid solvents, e.g. hydrochloric acid dissolved in an alkanol such as 1- or 2-propanol.

The compounds of formula (I) can also be prepared by forming the X linkage by either reacting (IV-a) with (V-a) or (IV-b) with (V-b) as outlined in the following scheme.

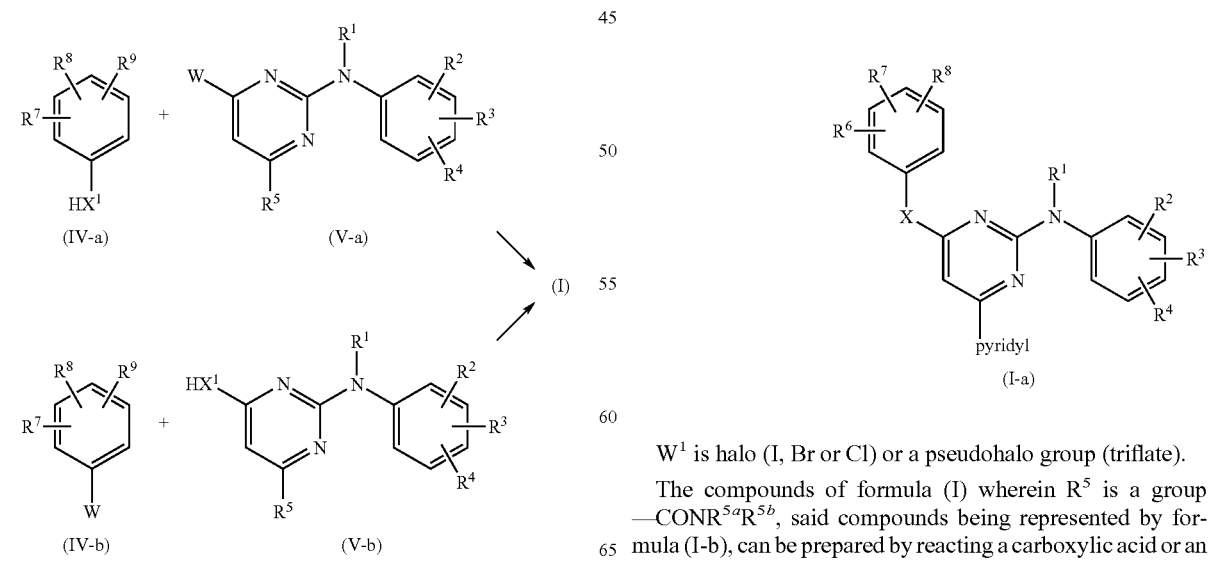

In this reaction scheme W represents an appropriate leaving group, which in particular is as specified above. The leaving group W in (V-a) may also be introduced in situ, e.g. by converting the corresponding hydroxy function into a leaving group for example by $POCl_3$. $X^1$ represents —$NR^1$—, —O—, —S—. Where $X^1$ is $NR^1$, the above reactions preferably are conducted in the presence of a tertiary amine base, e.g. triethylamine. Where $X^1$ represents O or S, the above reactions are conducted in the presence of a base such as for example $K_2CO_3$ or potassium t-butoxide (KOt-Bu).

In this reaction scheme W represents an appropriate leaving group, which in particular is as specified above. The leaving group W in (V-a) may also be introduced in situ, e.g. by converting the corresponding hydroxy function into a leaving group for example by $POCl_3$—Where X is $NR^1$, the above reactions preferably are conducted in the presence of a base, e.g. triethylamine.

Where X represents O or S, the above reactions are conducted in the presence of a suitable base, such as for example $K_2CO_3$ or potassium t-butoxide (KO t-Bu).

The compounds of formula (I) wherein $R^5$ is pyridyl, said compounds being represented by formula (I-a), can be prepared by a Suzuki reaction, i.e. by reacting a 6-halopyrimidine derivative (VI) with a pyridyl boric acid Het-B(OH)$_2$ or boric acid ester (in particular an alkyl ester such as methyl or ethyl ester) in the presence of a palladium catalyst, in particular Pd(PPh$_3$)$_4$.

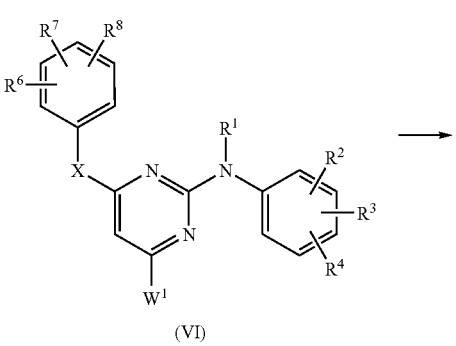

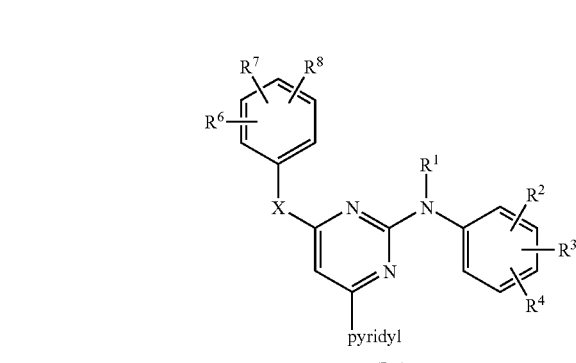

$W^1$ is halo (I, Br or Cl) or a pseudohalo group (triflate).

The compounds of formula (I) wherein $R^5$ is a group —CONR$^{5a}$R$^{5b}$, said compounds being represented by formula (I-b), can be prepared by reacting a carboxylic acid or an active form thereof (VII) with an amine (VIII), in an amide bond forming reaction.

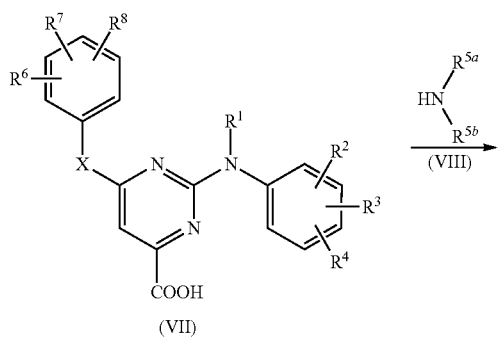

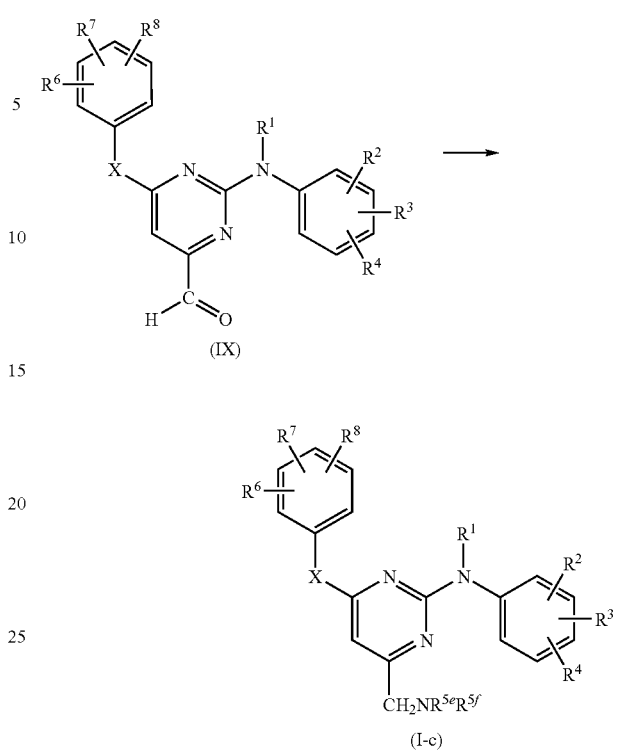

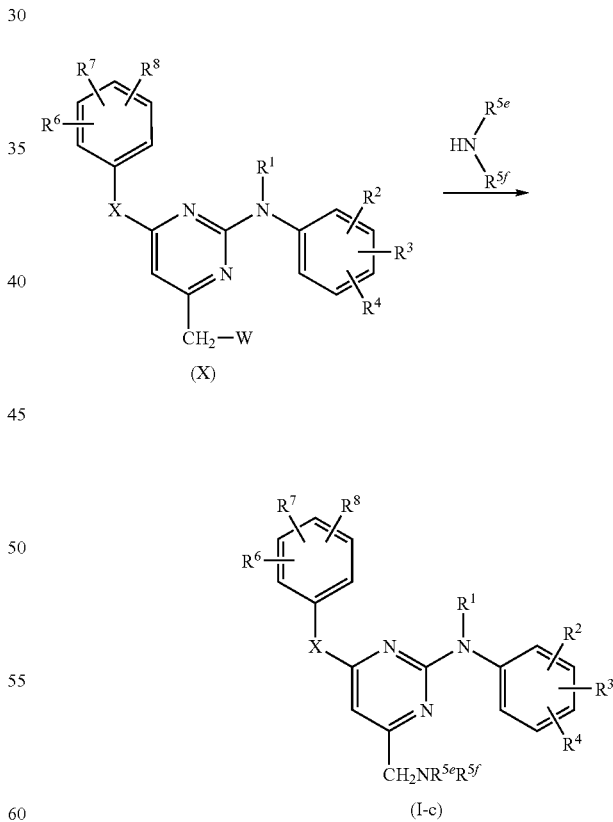

The amide bond forming reaction may be performed by reacting the starting materials in the presence of a coupling agent or by converting the carboxyl functionality in (VII) into an active form such as an active ester or carboxylic acid halides, in particular acid chlorides or bromides, azides, mixed carbonic-carboxylic acid anhydride (e.g. by reaction with isobutyl chloroformate), active esters (p-nitrophenyl ester, pentachloro-phenylester, N-hydroxysuccinic imido ester). The amines (VIII) may also be reacted with carboxylic acid lower alkyl esters, in particular the methyl or ethyl esters. Examples of coupling agents include the carbodiimides (dicyclohexylcarbodiimide, diisopropylcarbodiimide, or water-soluble carbodiimide such as N-ethyl-N'-[(3-dimethylamino)propyl]carbodiimide) or carbonyldiimidazoles. Some of these methods can be enhanced by adding suitable catalysts, e.g. in the carbodiimide method by adding 1-hydroxybenzotriazole or 4-dimethylaminopyridine (4-DMAP).

The amide bond forming reactions preferably are conducted in an inert solvent, such as halogenated hydrocarbons, e.g. dichloromethane, chloroform, dipolar aprotic solvents such as acetonitrile, dimethylformamide, dimethylacetamide, ethers such as tetrahydrofuran. In many instances the coupling reactions are done in the presence of a suitable base such as a tertiary amine, e.g. triethylamine, diisopropylethylamine (DIPEA), N-methylmorpholine, N-methylpyrrolidine, or 4-DMAP.

The compounds of formula (I) wherein $R^5$ is —$CH_2NR^{5e}R^{5f}$, said compounds being represented by formula (I-c), can be prepared by reductive amination reaction starting from the aldehydes (X). The reductive amination may be conducted with hydrogen in the presence of a noble metal catalyst such as Pt or Pd, or with a cyanoborohydride. These compounds can also be prepared by an N-alkylation reaction starting from intermediates (X), wherein W is specified above and in particular is chloro or bromo.

The compounds of formula (I-d), which are compounds of formula (I) wherein $R^5$ is —C(=O)—$R^{5d}$, can be prepared by reacting an intermediate (XI) with $R^{5d}$—H, which in particular is a heterocycle such as thiazole, in the presence of a strong base.

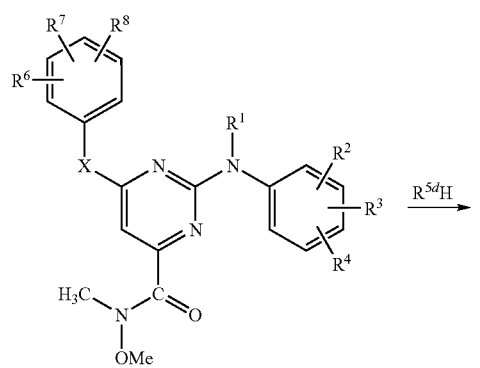

(XI)

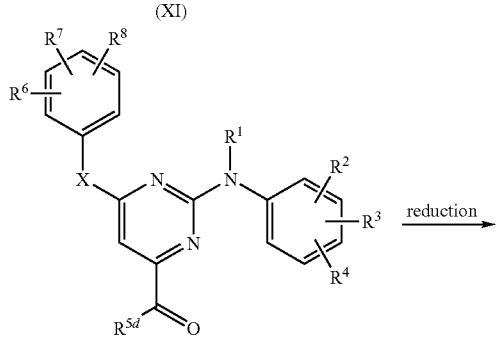

(I-d)

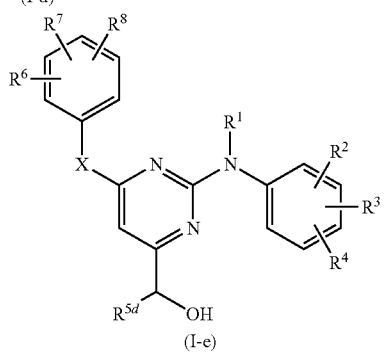

(I-e)

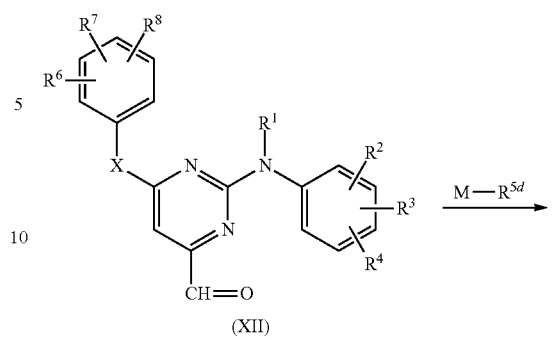

(XII)

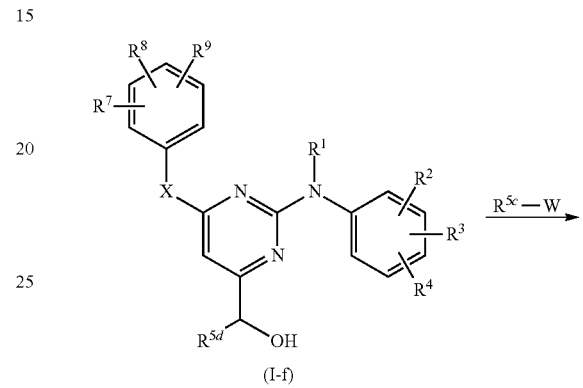

(I-f)

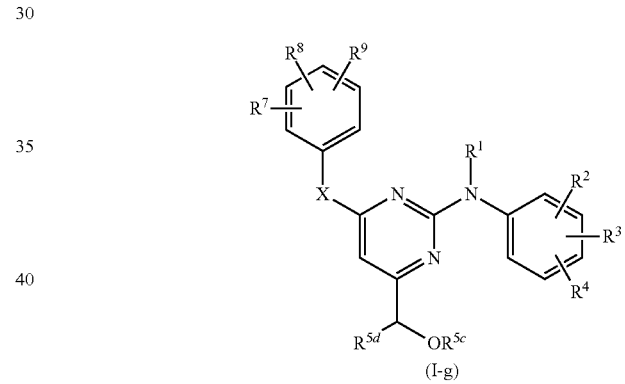

(I-g)

The compounds (I-d) may be reduced to the corresponding alcohols (I-e), for example with NaBH$_4$ in an alcohol such as methanol.

The compounds of formula (I-g), which are compounds of formula (I) wherein R$^5$ is —CH(OR$^{5c}$)R$^{5d}$, can be prepared by reacting a pyrimidine aldehyde of formula (XII) with an organo-metal compound (M-R$^{5d}$). The thus obtaining compounds of formula (I-f) can be converted to the corresponding compounds of formula (I-g), which are compounds of formula (I) wherein R$^{5c}$ is other than hydrogen. The group R$^{5c}$ can be introduced by an ether forming reaction such as an O-alkylation reaction with a reagent W$^1$—R$^{5c}$, wherein W$^1$ is a leaving group such as halo, in particular chloro, bromo or iodo, or a sulfate or azide group. M in M-R$^{5d}$ is a metal such as an alkali metal, in particular Li, Na or K, or a magnesium derivative such as a Grignard type of reagent (M-R$^{5d}$ is halo-Mg—R$^{5d}$). These reactions typically are conducted in a reaction-inert solvent such as an ether (THF, diethylether, dioxane) or a halogenated hydrocarbon (CH$_2$Cl$_2$, CHCl$_3$).

The compounds of formula (I-h), which are compounds of formula (I) wherein R$^5$ is —CH$_2$—OQ, wherein Q is —P(=O)(OR$^{5h}$)$_2$ or C$_{2-6}$alkenyl can be prepared by reacting (XII) with a dialkylchlorophosphate (XIII). This reaction is conducted in a reaction-inert solvent, e.g. THF, in the presence of a base, e.g. an alkali metal alkanolate, e.g. K-OtBu.

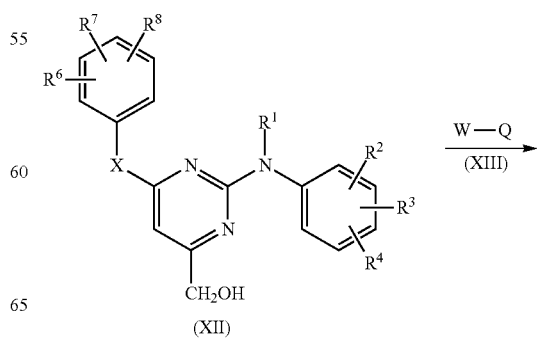

(XII)

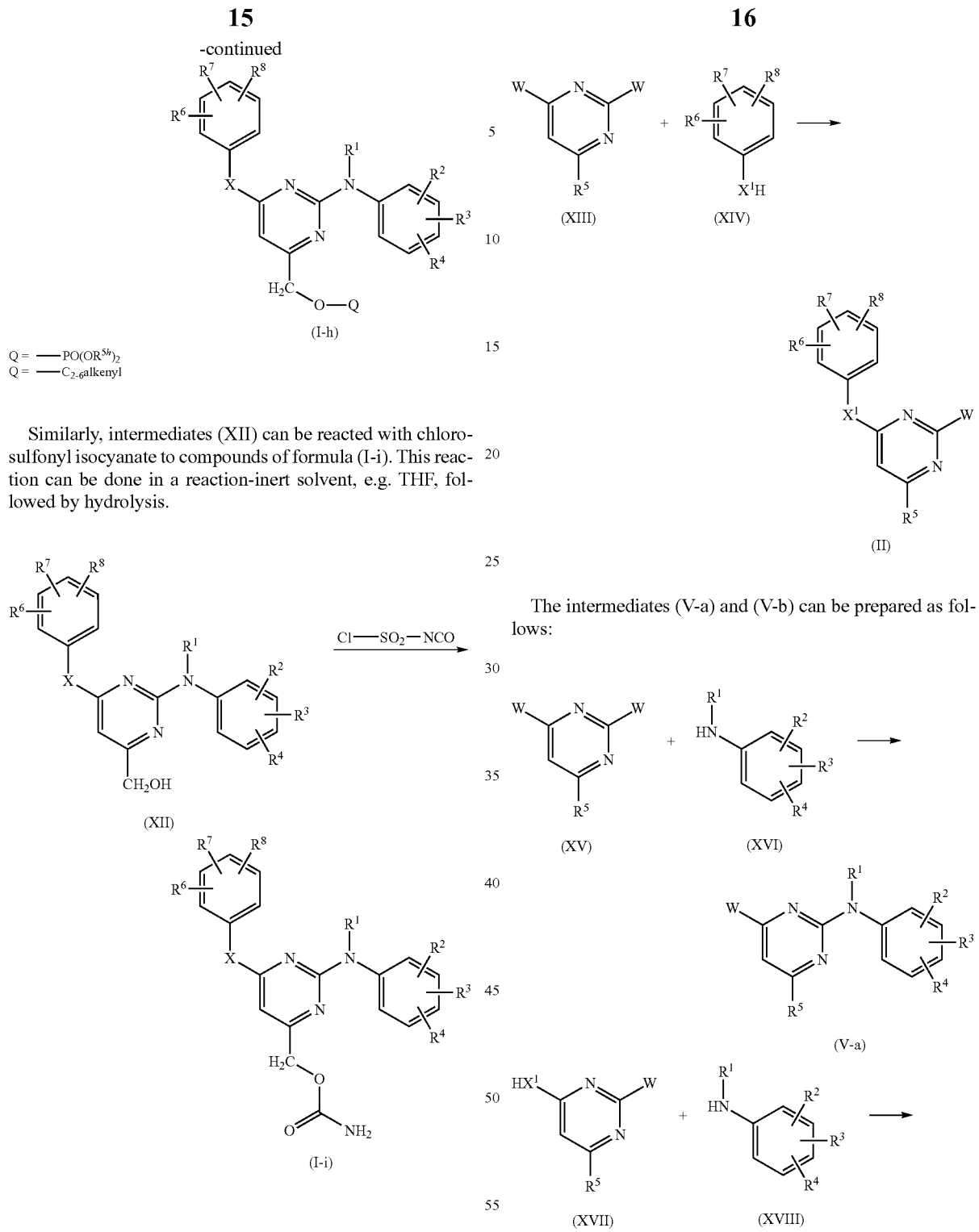

Similarly, intermediates (XII) can be reacted with chlorosulfonyl isocyanate to compounds of formula (I-i). This reaction can be done in a reaction-inert solvent, e.g. THF, followed by hydrolysis.

Some of the intermediates and starting materials are known compounds and may be commercially available or may be prepared according to art-known procedures.

Intermediates of formula (II) can be prepared by reacting an intermediate of formula (XIII) wherein each W is as defined hereinabove, with an intermediate of formula (XIV) in a suitable solvent, such as for example tetrahydrofuran, usually in the presence of a suitable base, such as for example $Na_2CO_3$. $X^1$ in the following schemes represents —$NR^1$—, —O—, or —S—.

The intermediates (V-a) and (V-b) can be prepared as follows:

The intermediates of formula (VII), (XI), and (XII) can be prepared as follows:

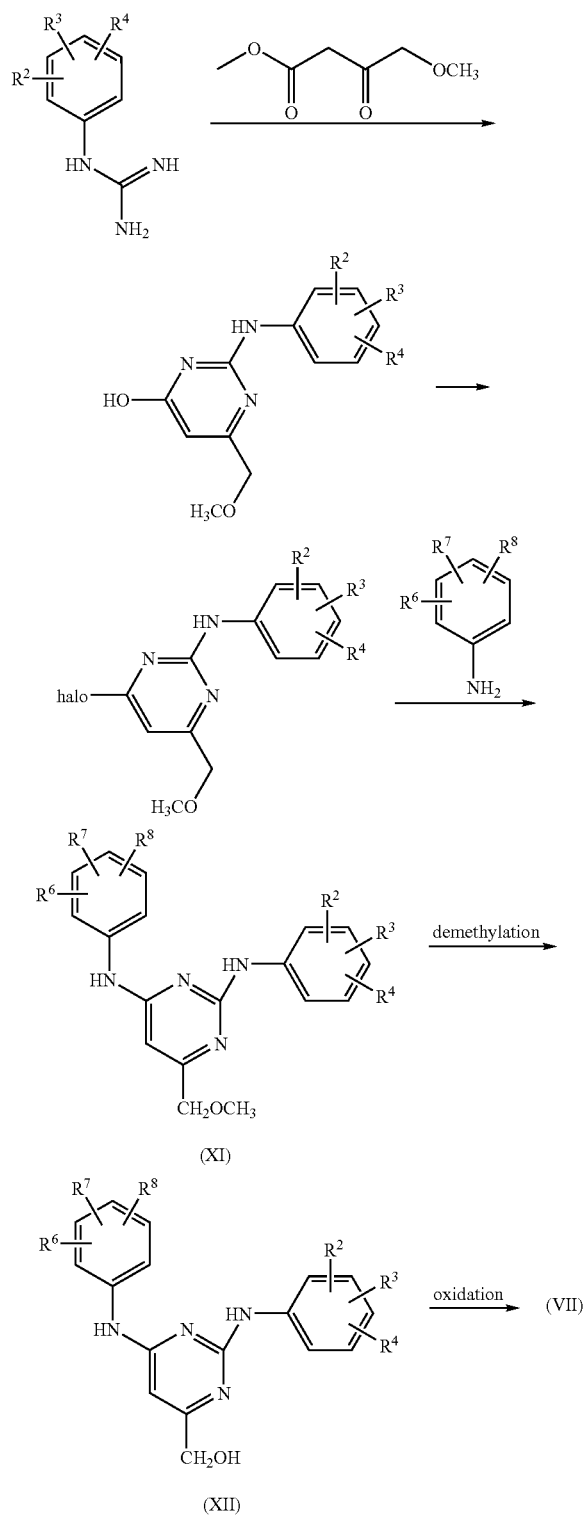

In a first step, an arylguanidine is condensed with 4-methoxyacetoacetic acid. The thus obtained hydroxypyrimidine is converted to the corresponding halopyrimidine using a halogenating agent such as POCl$_3$. The halo group is substituted by an aniline derivative to methoxymethyl derivative (XI). The latter is demethylated to methyl-alcohol (XII), which is oxidized to (VII).

Oxidation of (XII) with a mild oxidant such as MnO$_2$ in a reaction inert solvent such as acetone or dichloromethane yields intermediates (IX). Halogenation of (XII) such as by reaction with sulfonyl chloride in a reaction inert solvent such as THF or dichloromethane, yields intermediates (X).

The compounds of formula (I) may further be prepared by converting compounds of formula (I) into each other according to art-known group transformation reactions.

Compounds of formula (I) wherein $R^2$, $R^3$, $R^6$ or $R^7$ is hydrogen, can be converted into a compounds of formula (I) wherein $R^2$, $R^3$, $R^6$ or $R^7$ is halo by reaction with a suitable halo-introducing agent, such as for example N-chloro- or N-bromosuccinimide, in a suitable solvent, e.g. acetic acid. Compounds of formula (I) wherein $R^1$ represents $C_{1-6}$alkyloxycarbonyl, can be converted into a compound of formula (I) wherein $R^1$ represents hydrogen, by reaction with a suitable base, such as for example sodium hydroxide or methoxide. Where $R^1$ is t.butyloxycarbonyl, the corresponding compounds wherein $R^1$ is hydrogen can be made by treatment with trifluoroacetic acid.

Some of the compounds of formula (I) and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically. An alternative manner of separating the enantiomeric forms of the compounds of formula (I) and intermediates involves liquid chromatography, in particular liquid chromatography using a chiral stationary phase.

The compounds of formula (I) show antiretroviral properties (reverse transcriptase inhibiting properties), in particular against Human Immunodeficiency Virus (HIV), the aetiological agent of Acquired Immune Deficiency Syndrome (AIDS) in humans. The HIV virus preferentially infects human T-4 cells and destroys them or changes their normal function, particularly the coordination of the immune system. As a result, an infected patient has an ever-decreasing number of T-4 cells, which moreover behave abnormally. Hence, the immunological defense system is unable to combat infections and neoplasms and the HIV infected subject usually dies by opportunistic infections such as pneumonia, or by cancers. Other conditions associated with HIV infection include thrombocytopaenia, Kaposi's sarcoma and infection of the central nervous system characterized by progressive demyelination, resulting in dementia and symptoms such as, progressive dysarthria, ataxia and disorientation. HIV infection further has also been associated with peripheral neuropathy, progressive generalized lymphadenopathy (PGL) and AIDS-related complex (ARC).

The present compounds also show activity against drug- and multidrug-resistant HIV strains, in particular multidrug resistant HIV strains, more in particular the present compounds show activity against HIV strains that have acquired resistance to one or more art-known non-nucleoside reverse transcriptase inhibitors, in particular those that have been approved for therapy such as efavirenz, delavirdine, and nevirapine.

Due to their antiretroviral properties, particularly their anti-HIV properties, especially their anti-HIV-1-activity, the compounds of formula (I), the pharmaceutically acceptable addition salts, the pharmaceutically acceptable solvates thereof, or the possible stereoisomeric forms thereof, are useful in the treatment of individuals infected by HIV and for the prophylaxis of these infections. In general, the compounds of the present invention may be useful in the treatment of warm-blooded animals infected with viruses whose existence is mediated by, or depends upon, the enzyme reverse transcriptase. Conditions that may be prevented or treated with the compounds of the present invention, especially conditions associated with HIV and other pathogenic retroviruses, include AIDS, AIDS-related complex (ARC), progressive generalized lymphadenopathy (PGL), as well as chronic Central Nervous System diseases caused by retroviruses, such as, for example HIV mediated dementia and multiple sclerosis.

The compounds of the present invention or any subgroup thereof may therefore be used as medicines against above-mentioned conditions. Said use as a medicine or method of treatment comprises the administration to HIV-infected subjects of an amount effective to combat the conditions associated with HIV and other pathogenic retroviruses, especially HIV-1. In particular, the compounds of formula (I) may be used in the manufacture of a medicament for the treatment or the prevention of HIV infections.

In a further aspect this invention provides a method of treating warm-blooded animals, including humans, suffering from or a method of preventing warm-blooded animals, including humans, to suffer from viral infections, especially HIV infections. Said method comprises the administration, preferably oral administration, of an effective amount of a compound of formula (I), a pharmaceutically acceptable addition salt, a pharmaceutically acceptable solvate thereof, or a possible stereoisomeric form thereof, to warm-blooded animals, including humans.

The present invention also provides compositions for treating viral infections comprising a therapeutically effective amount of a compound of formula (I) and a pharmaceutically acceptable carrier or diluent.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions, and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared wherein the carrier comprises saline solution, glucose solution, or a mixture of saline and glucose solution. Injectable suspensions may also be prepared in which case appropriate liquid carriers, suspending agents and the like may be employed. Also included are solid form preparations that can be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

The compounds of the present invention may also be administered via inhalation or insufflation by means of methods and formulations employed in the art for administration via this way. Thus, in general the compounds of the present invention may be administered to the lungs in the form of a solution, a suspension or a dry powder. Any system developed for the delivery of solutions, suspensions or dry powders via oral or nasal inhalation or insufflation are suitable for the administration of the present compounds.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of HIV-infection could determine the effective daily amount from the test results presented here. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines and are not intended to limit the scope or use of the invention to any extent.

The present compounds of formula (I) can be used alone or in combination with other therapeutic agents, such as anti-virals, antibiotics, immunomodulators or vaccines for the treatment of viral infections. They may also be used alone or in combination with other prophylactic agents for the prevention of viral infections. The present compounds may be used in vaccines and methods for protecting individuals against viral infections over an extended period of time. The compounds may be employed in such vaccines either alone or together with other compounds of this invention or together with other anti-viral agents in a manner consistent with the conventional utilization of reverse transcriptase inhibitors in vaccines. Thus, the present compounds may be combined with pharmaceutically acceptable adjuvants conventionally employed in vaccines and administered in prophylactically effective amounts to protect individuals over an extended period of time against HIV infection.

Also, the combination of one or more additional antiretroviral compounds and a compound of formula (I) can be used as a medicine. Thus, the present invention also relates to a product containing (a) a compound of formula (I), and (b) one or more additional antiretroviral compounds, as a combined preparation for simultaneous, separate or sequential use in anti-HIV treatment. The different drugs may be combined in a single preparation together with pharmaceutically acceptable carriers. Said other antiretroviral compounds may be any known antiretroviral compounds such as suramine, pentamidine, thymopentin, castanospermine, dextran (dextran sulfate), foscarnet-sodium (trisodium phosphono formate); nucleoside reverse transcriptase inhibitors (NRTIs), e.g. zidovudine (AZT), didanosine (ddI), zalcitabine (ddC), lamivudine (3TC), stavudine (d4T), emtricitabine (FTC), abacavir (ABC), amdoxovir (DAPD), elvucitabine (ACH-126, 443), AVX 754 ((−)-dOTC), fozivudine tidoxil (FZT), phosphazide, HDP-990003, KP-1461, MIV-210, racivir (PSI-5004), UC-781 and the like; non-nucleoside reverse transcriptase inhibitors (NNRTIs) such as delavirdine (DLV), efavirenz (EFV), nevirapine (NVP), dapivirine (TMC120), etravirine (TMC125), rilpivirine (TMC278), DPC-082, (+)-Calanolide A, BILR-355, and the like; nucleotide reverse transcriptase inhibitors (NtRTIs), e.g. tenofovir ((R)-PMPA) and tenofovir disoproxil fumarate (TDF), and the like; nucleotide-competing reverse transcriptase inhibitors (NcRTIs), e.g. NcRTI-1 and the like; inhibitors of trans-activating proteins, such as TAT-inhibitors, e.g. RO-5-3335, BI-201, and the like; REV inhibitors; protease inhibitors e.g. ritonavir (RTV), saquinavir (SQV), lopinavir (ABT-378 or LPV), indinavir (IDV), amprenavir (VX-478), TMC126, nelfinavir (AG-1343), atazanavir (BMS 232,632), darunavir (TMC114), fosamprenavir (GW433908 or VX-175), brecanavir (GW-640385, VX-385), P-1946, PL-337, PL-100, tipranavir (PNU-140690), AG-1859, AG-1776, Ro-0334649 and the like; entry inhibitors which comprise fusion inhibitors (e.g. enfuvirtide (T-20)), attachment inhibitors and co-receptor inhibitors, the latter comprise the CCR5 antagonists (e.g. ancriviroc, CCR5 mAb004, maraviroc (UK-427,857), PRO-140, TAK-220, TAK-652, vicriviroc (SCH-D, SCH-417, 690)) and CXCR4 antagonists (e.g. AMD-070, KRH-27315), examples of entry inhibitors are PRO-542, TNX-355, BMS-488,043, BlockAide/CR™, FP 21399, hNM01, nonakine, VGV-1; a maturation inhibitor for example is PA-457; inhibitors of the viral integrase e.g. raltegravir (MK-0518), elvitegravir (JTK-303, GS-9137), BMS-538,158; ribozymes; immunomodulators; monoclonal antibodies; gene therapy; vaccines; siRNAs; antisense RNAs; microbicides; Zinc-finger inhibitors.

The combination may provide a synergistic effect, whereby viral infectivity and its associated symptoms may be prevented, substantially reduced, or eliminated completely.

The compounds of the present invention may also be administered in combination with immunomodulators (e.g., bropirimine, anti-human alpha interferon antibody, IL-2, methionine enkephalin, interferon alpha, and naltrexone), with antibiotics (e.g. pentamidine isothiorate), cytokines (e.g. Th2), modulators of cytokines, chemokines or modulators of chemokines, chemokine receptors (e.g. CCR5, CXCR4), modulators of chemokine receptors, or hormones (e.g. growth hormone) to ameliorate, combat, or eliminate HIV infection and its symptoms. Such combination therapy in different formulations may be administered simultaneously, sequentially or independently of each other. Alternatively, such combination may be administered as a single formulation, whereby the active ingredients are released from the formulation simultaneously or separately.

The compounds of the present invention may also be administered in combination with modulators of the metabolization following application of the drug to an individual. These modulators include compounds that interfere with the metabolization at cytochromes, such as cytochrome P450. It is known that several isoenzymes exist of cytochrome P450, one of which is cytochrome P450 3A4. Ritonavir is an example of a modulator of metabolization via cytochrome P450. Such combination therapy in different formulations may be administered simultaneously, sequentially or independently of each other. Alternatively, such combination may be administered as a single formulation, whereby the active ingredients are released from the formulation simultaneously or separately. Such modulator may be administered at the same or different ratio as the compound of the present invention. Preferably, the weight ratio of such modulator vis-à-vis the compound of the present invention (modulator:compound of the present invention) is 1:1 or lower, more preferable the ratio is 1:3 or lower, suitably the ratio is 1:10 or lower, more suitably the ratio is 1:30 or lower.

Although the present invention focuses on the use of the present compounds for preventing or treating HIV infections, the present compounds may also be used as inhibitory agents for other viruses that depend on reverse transcriptases for multiplication.

The following examples are intended to illustrate the present invention and not to limit its scope thereto.

EXAMPLE 1

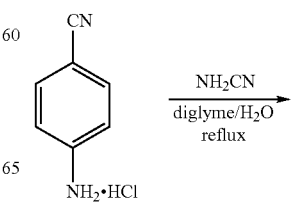

-continued

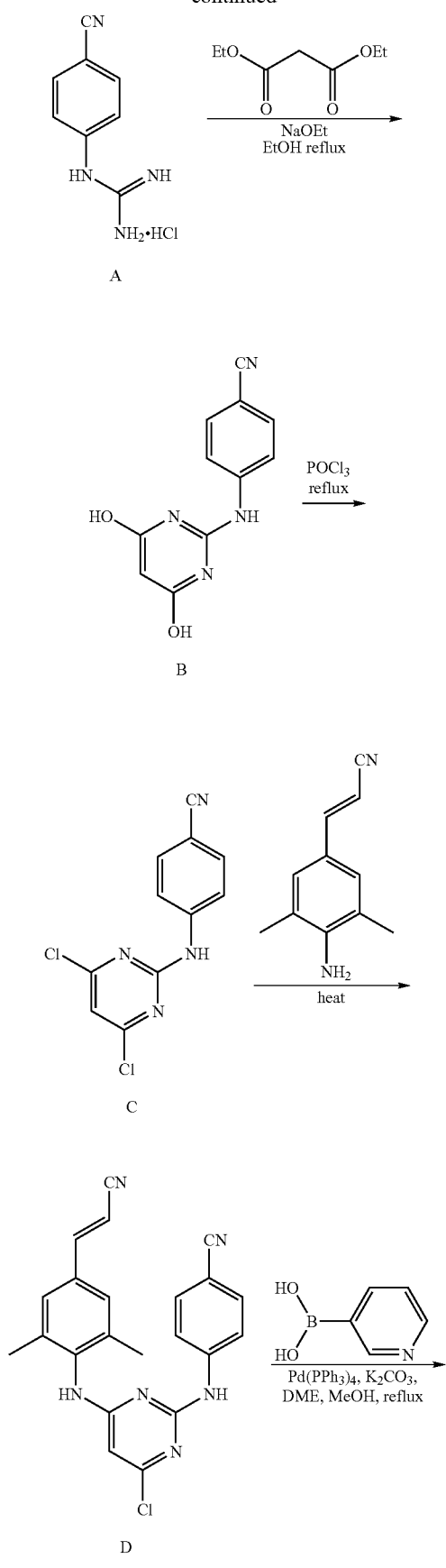

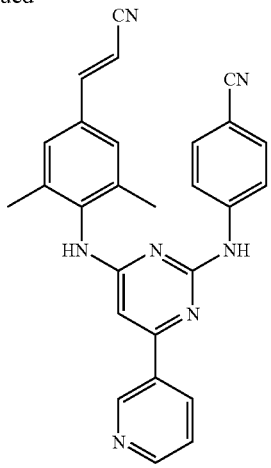

A mixture of 4-cyanoaniline (0.420 mol) in 2-methoxyethyl ether (250 ml) was stirred at 100° C. for 30 min. Then a mixture of cyanamide (0.630 mol) in water (30 ml) was added portion wise during 45 min. After stirring 24 hours at 100° C., cyanamide (0.210 mol) was added again. The mixture was then stirred at 100° C. for an additional 48 hours and subsequently evaporated until dryness. The residue crystallized from acetone yielding 70.5 g of intermediate A (85% yield, melting point: 225° C.).

To a solution of A (0.0102 mol) in ethanol (25 ml) was added sodium ethoxide (21%) (0.0153 mol, 1.5 eq.), followed by malonic acid diethyl ester (0.0102 mol, 1 eq.). The resulting mixture was stirred at reflux for 6 hours and then allowed to cool down to room temperature. Water was added and the mixture acidified with acetic acid (until pH=6). The resulting precipitate was filtered to give 1.5 g of desired compound B (57% yield).

A mixture of B (0.0056 mol) and phosphorus oxychloride (10 ml) was stirred at reflux for 30 min. After cooling down, phosphorus oxychloride was evaporated. Water and $K_2CO_3$ 10% were added and the mixture was extracted with $CH_2Cl_2$. The organic layer was dried over magnesium sulfate, filtered and the solvent evaporated to give 1.51 g of C (97% yield).

3-(4-Amino-3,5-dimethylphenyl)-acrylonitrile (0.00754 mol) and the dichloropyrimidine C (0.00754 mol) was mixed and heated until fusion. The mixture was poured in water and $K_2CO_3$ 10% and extracted with $CH_2Cl_2$ and methanol. The organic layer was dried over magnesium sulfate, filtered and the solvent evaporated. The residue was purified by column chromatography over silica gel (35-70 µm; eluent: $CH_2Cl_2$/methanol 99.5:0.5). The fractions with the desired compound were collected and the solvent evaporated to give 0.4 g of intermediate D with 72% purity (9% yield).

A mixture of intermediate D (0.0003 mol), triphenylphosphine palladium (0.00006 mol), $K_2CO_3$ 2M (0.001 mol) and pyridyl-3-boronic acid (0.0009 mol) in dimethoxyethane (DME; 5 ml) and methanol (1 ml) was stirred at reflux overnight. After cooling, the mixture was filtered over celite and the filtrate poured in water and extracted with $CH_2Cl_2$. The organic layer was dried over magnesium sulfate, filtered and the solvent evaporated. The residue was purified by column chromatography over silica gel (Kromasil 5 µm; eluent: $CH_2Cl_2$ 100 to $CH_2Cl_2$/methanol 99:1). The pure fractions were collected and the solvent evaporated to give 0.042 g of pure product compound 1 (15% yield, melting point: 180° C., E/Z 97/3).

EXAMPLE 2

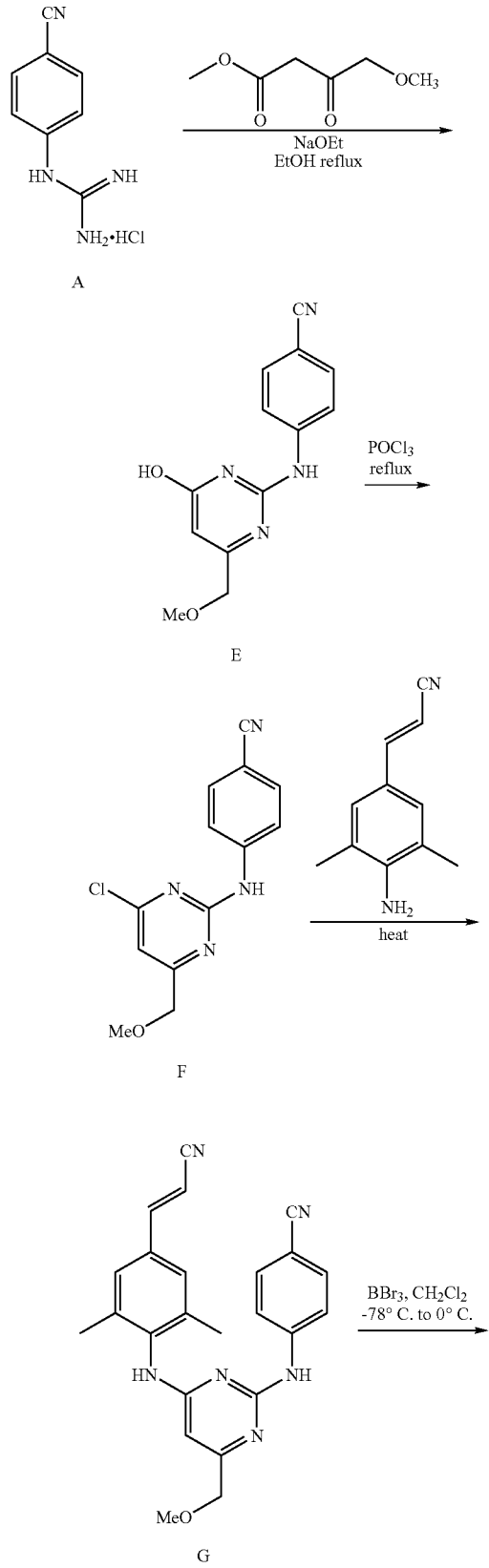

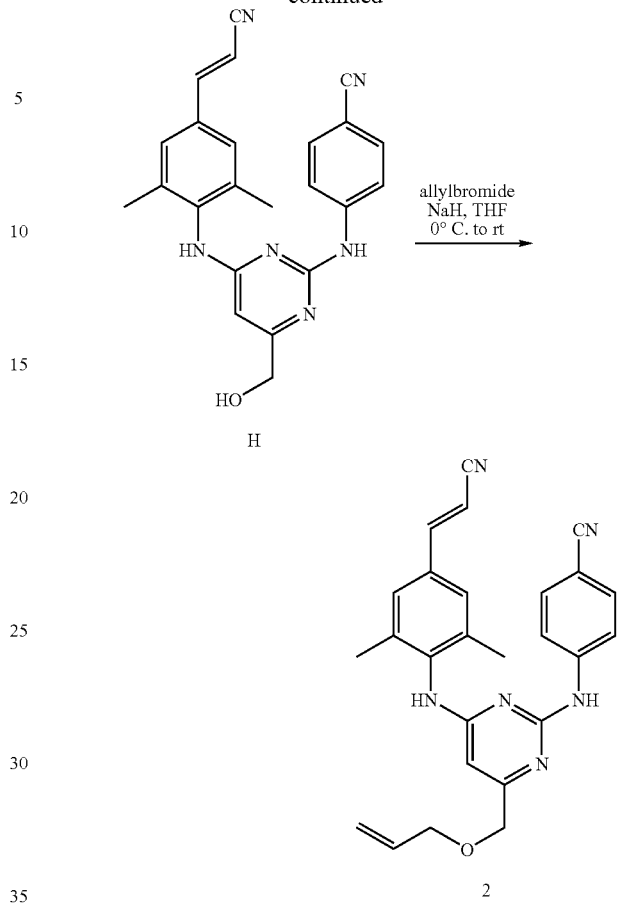

To a solution of intermediate A (0.0102 mol), prepared as in example 1, in ethanol (25 ml) was added sodium ethoxide (21%) (0.0153 mol, 1.5 eq.) followed by methyl 4-methoxyacetoacetate (0.0102 mol, 1 eq.). The resulting mixture was stirred at reflux for 6 hours and then allowed to cool down to room temperature. Water was added and the mixture acidified with acetic acid (until pH=6). The resulting precipitate was filtered to give 1.5 g of intermediate E (57% yield).

A mixture of E (0.0056 mol) and phosphorus oxychloride (10 ml) was stirred at reflux for 30 min. After cooling down, phosphorus oxychloride was evaporated. Water and $K_2CO_3$ 10% were added and the mixture was extracted with $CH_2Cl_2$. The organic layer was dried over magnesium sulfate, filtered and the solvent evaporated to give 1.51 g of F (97% yield).

A mixture of intermediate F (0.00182 mol) and 3-(4-amino-3,5-dimethylphenyl)acrylonitrile (0.00182 mol) were heated until fusion for 5 minutes, then poured in a mixture of water and $K_2CO_3$ 10%. The resulting mixture was extracted with $CH_2Cl_2$. The organic layer was dried over magnesium sulfate, filtered and the solvent evaporated. The residue was purified by column chromatography over silica gel (35-70 μm; eluent: $CH_2Cl_2$/methanol 97:3). The pure fractions were collected and the solvent evaporated to give 0.34 g of intermediate G (46% yield, melting point: 115° C.).

Boron tribromide 1 M in $CH_2Cl_2$ (0.00456 mol) was added drop wise to a solution of the methoxy derivative G (0.000828 mol) in $CH_2Cl_2$ (15 ml) at −78° C. The solution was stirred at −78° C. for 20 min and at 0° C. for 3 h. Ice was added and the mixture was extracted with $CH_2Cl_2$. The organic layer was dried over magnesium sulfate, filtered and the solvent evaporated. The residue was crystallized from $CH_2Cl_2$ giving 0.22 g of intermediate H (67% yield, melting point: 232° C.).

Sodium hydride (60% in oil, 0.0006 mol, 1.2 eq.) was added to an ice-cooled mixture of methyl alcohol derivative H (0.0005 mol) and allylbromide (0.0006 mol, 1.2 eq.) in tetrahydrofuran (THF; 5 ml). After 30 min at 0° C., the mixture was allowed to warm up to room temperature and stirred for 42 hours. Water was added and the mixture was extracted with $CH_2Cl_2$. The organic layer was dried over magnesium sulfate, filtered and the solvent evaporated. The residue was purified by column chromatography over silica gel (5 µm, eluent: $CH_2Cl_2$/methanol/$NH_4OH$ 99:1:0.1 to 90:10:1) to give 0.074 g of pure compound 2 (34% yield, melting point: 111° C.).

ml) and the mixture was stirred at room temperature for 5 h, then filtered over celite. The celite was washed with $CH_2Cl_2$/methanol and the filtrate was evaporated. The residue was crystallized from $CH_2Cl_2$ and a few drops of methanol. The precipitate afforded the acid derivative J (0.63 g, 45% yield). The filtrate was evaporated and the residue afforded the aldehyde I (0.55 g, 46% yield). These two compounds were engaged in the next steps without further purification.

EXAMPLE 3

EXAMPLE 4

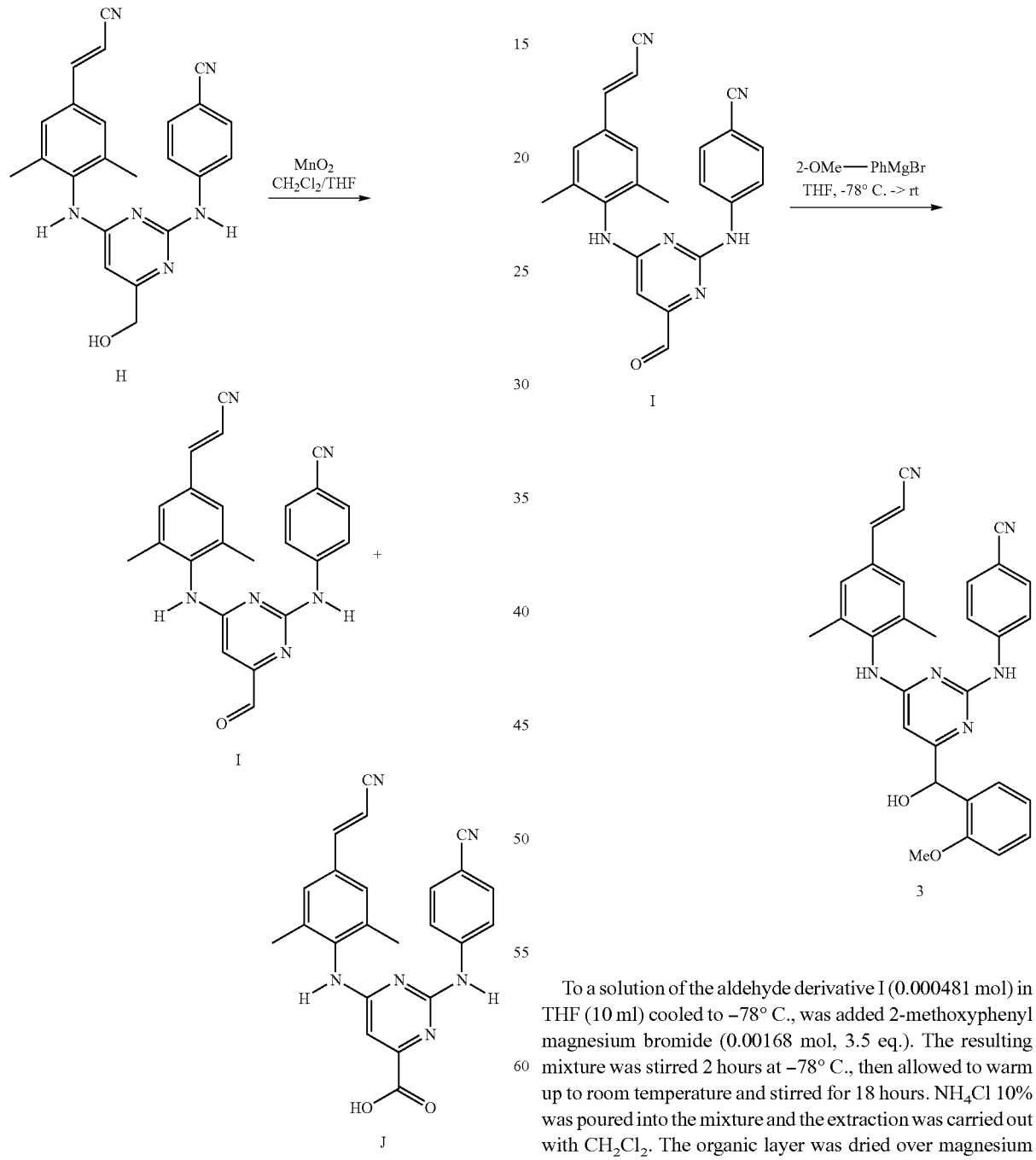

Manganese oxide (0.0345 mol) was added to a solution of intermediate H (0.00343 mol) in $CH_2Cl_2$ (70 ml) and THF (20

To a solution of the aldehyde derivative I (0.000481 mol) in THF (10 ml) cooled to −78° C., was added 2-methoxyphenyl magnesium bromide (0.00168 mol, 3.5 eq.). The resulting mixture was stirred 2 hours at −78° C., then allowed to warm up to room temperature and stirred for 18 hours. $NH_4Cl$ 10% was poured into the mixture and the extraction was carried out with $CH_2Cl_2$. The organic layer was dried over magnesium sulfate, filtered and the solvent evaporated. The residue was purified by column chromatography over silica gel (Kromasil™ 5 µm; eluent: $CH_2Cl_2$/methanol 100:0 to 96:4). The pure fractions were collected and the solvent evaporated, yielding 0.026 g of compound 3 (11% yield).

EXAMPLE 5

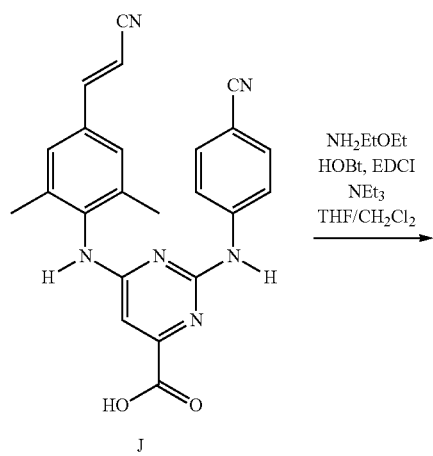

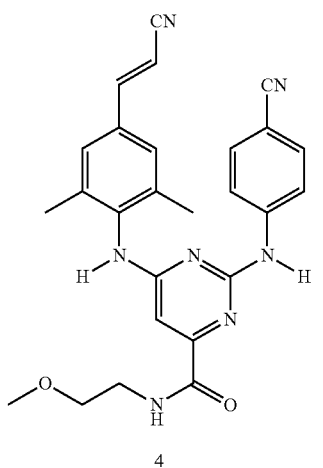

1-hydroxybenzotriazole (0.000366 mol, 1.5 eq.) was added to a mixture of the acid J (0.000244 mol) in THF (3 ml). Dichloromethane (3 ml) and 1-(3-dimethylaminopropyl)-3-ethylcarbodiimide hydrochloride (0.000366 mol, 1.5 eq.) were added successively to the mixture. To this solution, was added 2-ethoxyethylamine (0.000366 mol, 1.5 eq.) followed by triethylamine (0.000488 mol, 2 eq.). The mixture was stirred at room temperature for 24 h then poured in water and $K_2CO_3$ 10% and extracted with a 90:10 mixture of $CH_2Cl_2$/methanol. The organic layer was dried over magnesium sulfate, filtered and the solvent evaporated. The residue was purified by column chromatography over silica gel (Kromasil™ 5 μm; eluent: $CH_2Cl_2$/methanol 100:0 to 97:3), yielding 0.057 g of compound 4 (50% yield, melting point: 130° C.).

In this and the following tables, the bond marked ⊥ represents the bond linking the radical to the remainder of the molecule. Me and Et refer to methyl and ethyl respectively.

TABLE 1

| Compound No. | R | |
|---|---|---|
| 4 | methoxyethyl | E/Z 90/10 mp 130° C. 50% yield |
| 5 | fluoropropyl | E mp >250° C. 36% yield |
| 6 | cyanopropyl | E/Z 92/8 mp 250° C. 47% yield |
| 7 | pyridin-3-ylmethyl | E/Z 90/10 mp 202° C. 40% yield |
| 8 | furan-2-ylmethyl | E/Z 88/12 mp 256° C. 58% yield |

EXAMPLE 6

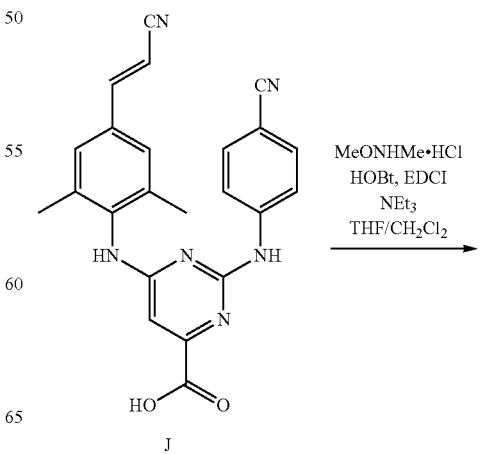

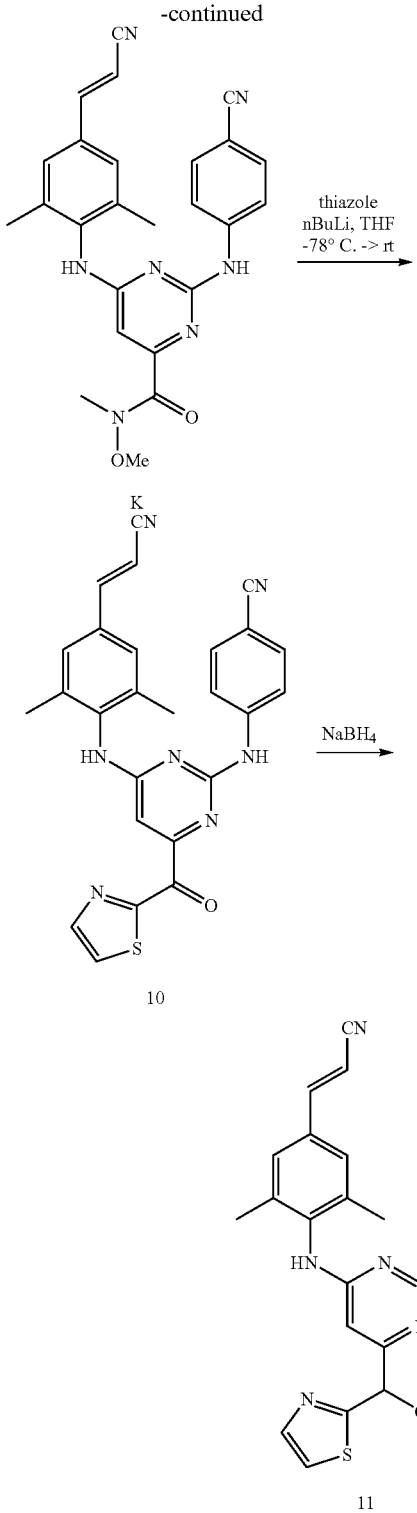

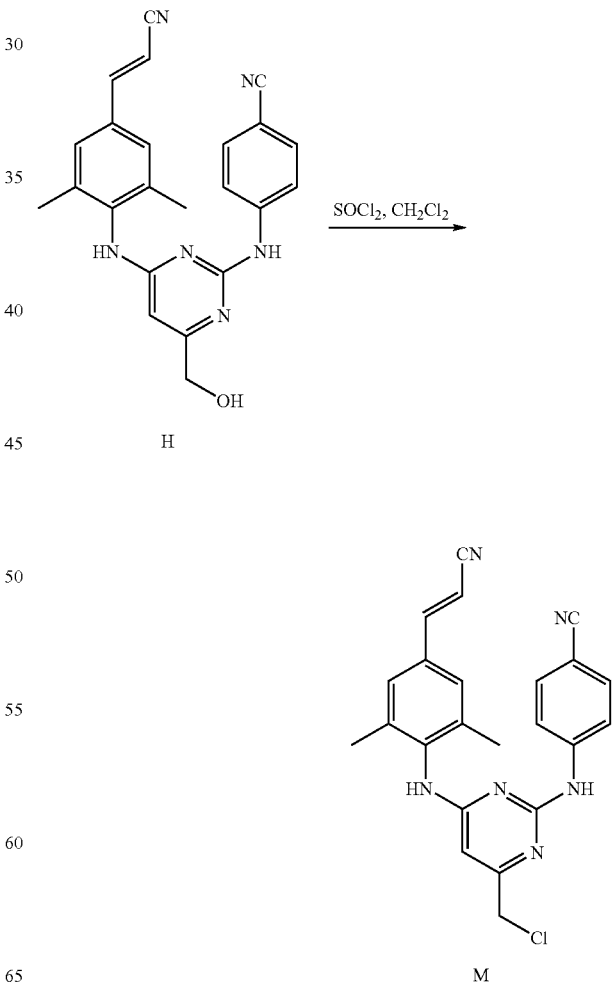

sulfate, filtered and the solvent evaporated. The obtained intermediate K was then engaged in the next steps without further purification.

To a solution of thiazole (0.003 mol, 5 eq.) in THF (2.5 ml) at −78° C. was added drop wise n-butyllithium (0.003 mol, 5 eq.); the resulting mixture was stirred at −78° C. for 25 min before adding drop wise a solution of intermediate K (0.0006 mol) in THF (6 ml). The resulting mixture was allowed to warm up to room temperature and stirring was maintained overnight. 10% $NH_4Cl$ was added to the mixture, and this was extracted then with $CH_2Cl_2$. The organic layer was dried over magnesium sulfate, filtered and the solvent evaporated. The residue was purified by column chromatography over silica gel (3.5 μm; eluent: $CH_2Cl_2$/methanol/$NH_4OH$ 100:0:0 to 96:4:0.4) giving 0.017 g of compound 10 (6% yield).

To an ice-cooled solution of compound 10 (0.0013 mol) in methanol (5 ml) was added sodium borohydride (0.0007 mol, 0.55 eq.); the resulting mixture was stirred at 0° C. for 2.5 hours. 10% $NH_4Cl$ was added to the mixture extracted then with $CH_2Cl_2$. The organic layer was dried over magnesium sulfate, filtered and the solvent evaporated. The residue was purified by column chromatography over silica gel (3.5 μm; eluent: $CH_2Cl_2$/methanol/$NH_4OH$ 99:1:0.1 to 94:6:0.6) to give 0.095 g of compound 11 (15% yield, melting point: 147° C.).

EXAMPLE 7

1-Hydroxybenzotriazole (0.0009 mol, 1.5 eq.) was added to a mixture of the acid J (0.0006 mol) in THF (3 ml). Dichloromethane (3 ml) and 1-(3-dimethylaminopropyl)-3-ethylcarbodiimide hydrochloride (0.0009 mol, 1.5 eq.) were added successively to the mixture. To this solution, was added N,O-dimethylhydroxylamine hydrochloride (0.0009 mol, 1.5 eq.) followed by triethylamine (0.0009 mol, 1.5 eq.). The mixture was stirred at room temperature for 36 h then poured in water and $K_2CO_3$ 10% and extracted with a 90:10 mixture of $CH_2Cl_2$/THF. The organic layer was dried over magnesium To an ice-cooled solution of the methyl alcohol derivative H (0.004 mol) in CH$_2$Cl$_2$ (16 ml) was added drop wise thionyl chloride (8.5 ml). The mixture was stirred at 5° C. for 2 hours. The solvent was evaporated to give a yellow powder, next dried under vacuum at 60° C. to afford 1.65 g of intermediate M used without further purification in the next steps (99% yield).

Method A:

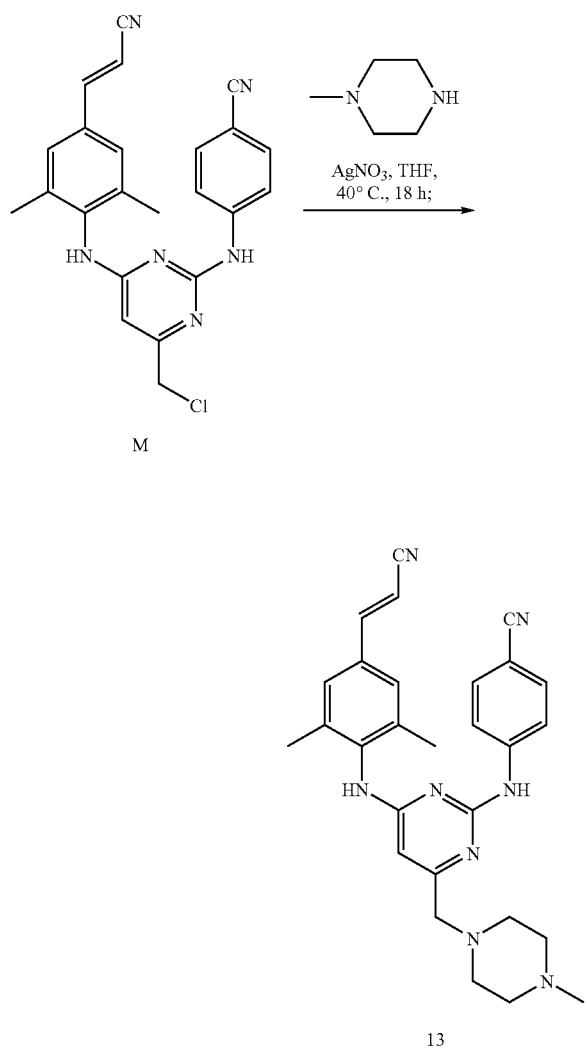

Method B:

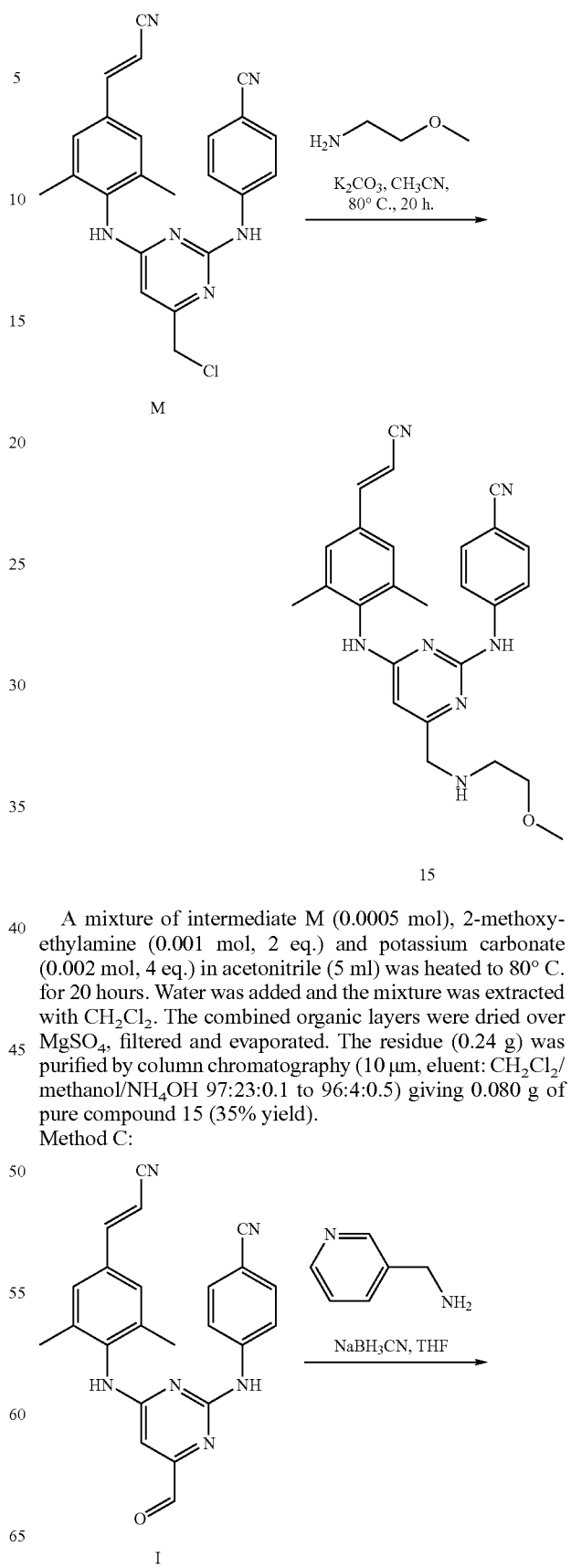

A mixture of intermediate M (0.0005 mol), 2-methoxy-ethylamine (0.001 mol, 2 eq.) and potassium carbonate (0.002 mol, 4 eq.) in acetonitrile (5 ml) was heated to 80° C. for 20 hours. Water was added and the mixture was extracted with CH$_2$Cl$_2$. The combined organic layers were dried over MgSO$_4$, filtered and evaporated. The residue (0.24 g) was purified by column chromatography (10 μm, eluent: CH$_2$Cl$_2$/methanol/NH$_4$OH 97:23:0.1 to 96:4:0.5) giving 0.080 g of pure compound 15 (35% yield).

Method C:

To a solution of intermediate M (0.0006 mol) in THF (5 ml) was added silver nitrate (0.0072 mol, 1.2 eq.) followed after 5 min of stirring by 1-methylpiperazine (0.0072 mol, 1.2 eq.). The whole was stirred at 40° C. overnight. Water was then added and the mixture was filtered over a celite pad and washed with CH$_2$Cl$_2$. The residue was extracted with CH$_2$Cl$_2$ and the combined organic layers were washed with 10% NH$_4$Cl solution, dried over MgSO$_4$ and filtered. The solvent was evaporated and the resulting mixture (0.345 g) was purified by column chromatography (5 μm, eluent: CH$_2$Cl$_2$/methanol/NH$_4$OH 98:2:0.2 to 92:8:0.8) giving 0.122 g of pure compound 13 (43% yield).

-continued

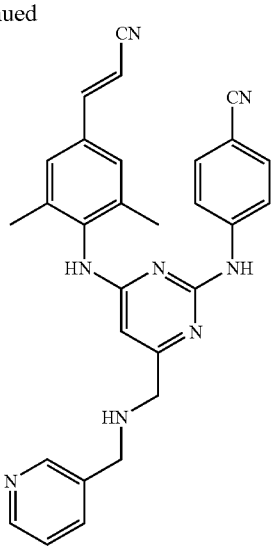

27

Two drops of acetic acid were added at room temperature to a mixture of sodium cyanoborohybride (0.00152 mol), the aldehyde I (0.000508 mol), and 3-(aminomethyl)pyridine (0.000761 mol) in THF (10 ml). The mixture was stirred at room temperature for 4 hours. The mixture was poured in water and $K_2CO_3$ 10% and extracted with $CH_2Cl_2$. The organic layer was dried over magnesium sulfate, filtered and the solvent evaporated. The residue was purified by column chromatography over silica gel (Kromasil 5 μm; eluent: $CH_2Cl_2$/methanol/$NH_4OH$ 99:1:0.05 to 95:5:0.25). The pure fractions were collected and the solvent evaporated. The residue was crystallized from diethyl ether to give 0.063 g of pure compound 27 (26% yield, melting point: 180° C.).

TABLE 2

| Compound No | Method | —NR$^{5e}$R$^{5f}$ | |
|---|---|---|---|
| 12 | A | —N(morpholine) | E/Z 90/10<br>mp 136° C.<br>40% yield |
| 13 | A | —N(piperazine)N— | E<br>mp 126° C.<br>43% yield |
| 14 | B | —NH—CH$_2$-cyclopropyl | E/Z 87/13<br>mp -<br>22% yield |
| 15 | B | —NH—CH$_2$CH$_2$—O—CH$_3$ | E/Z 87/13<br>mp 99° C.<br>35% yield |

TABLE 2-continued
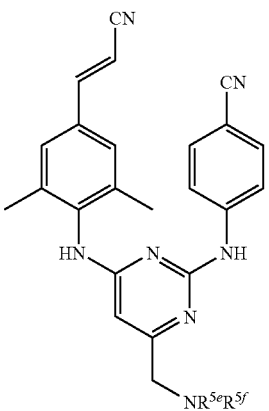
| Compound No | Method | —NR^{5e}R^{5f} | |
|---|---|---|---|
| 16 | B | 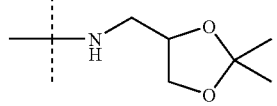 | E/Z 85/15<br>mp -<br>24% yield |
| 17 | B | 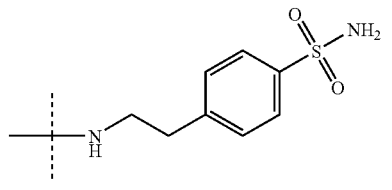 | E/Z 85/15<br>mp -<br>27% yield |
| 18 | B | 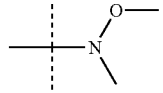 | E/Z 85/15<br>mp -<br>10% yield |
| 19 | B | 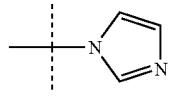 | E/Z 85/15<br>mp 152° C.<br>18% yield |
| 20 | B | 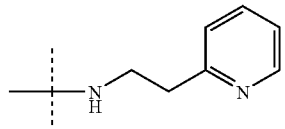 | E/Z 85/15<br>mp 143° C.<br>17% yield |
| 21 | B | 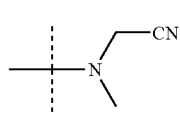 | mp -<br>9% yield |
| 22 | B | 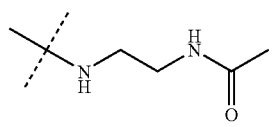 | E/Z 84/16<br>mp -° C.<br>?% yield |
| 23 | B | 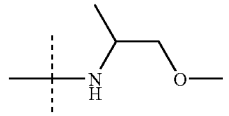 | E/Z 80/20<br>mp -<br>25% yield |
| 24 | B | 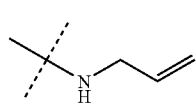 | E/Z 75/25<br>mp 112° C.<br>17% yield |

TABLE 2-continued

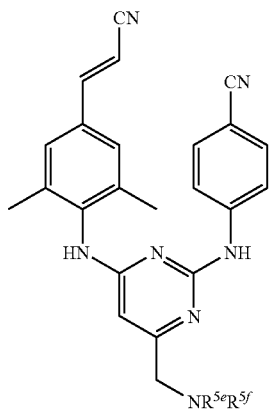

| Compound No | Method | —NR^{5e}R^{5f} | |
|---|---|---|---|
| 25 | C | (pyridin-2-ylmethyl)amino- | E/Z 87/13<br>mp 124° C.<br>13% yield |
| 26 | C | (furan-2-ylmethyl)amino- | E/Z 88/12<br>mp 149° C.<br>22% yield |
| 27 | C | (pyridin-3-ylmethyl)amino- | E/Z 88/12<br>mp 180° C.<br>26% yield |
| 28 | C | (tetrahydrofuran-2-ylmethyl)amino- | E/Z 80/20<br>mp 126° C.<br>29% yield |
| 29 | C | (3-morpholinopropyl)amino- | E/Z 80/20<br>mp 120° C.<br>27% yield |
| 30 | C | (pyridin-4-ylmethyl)amino- | E/Z 85/15<br>mp 218° C.<br>64% yield |
| 31 | C | (thiophen-2-ylmethyl)amino- | E/Z 85/15<br>mp 128° C.<br>30% yield |

EXAMPLE 8

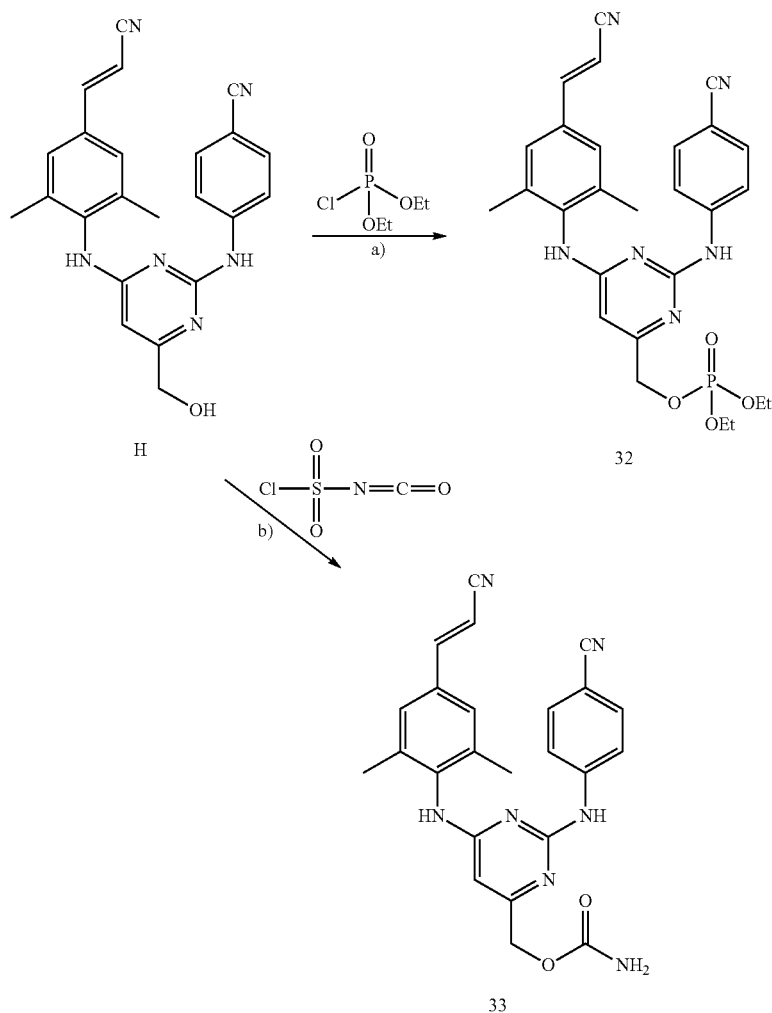

a) tBuOK, THF, 0° C. then RT, 1 h;
b) THF, H₂O, -78° C. then 70° C., 15 h;

To an ice-cooled mixture of potassium tert-butoxide (0.000416 mol) in THF, was added the methyl alcohol derivative H (0.000378 mol) followed by diethyl chlorophosphate (0.000416 mol). The mixture was stirred at room temperature for 1 h and then poured into water and extracted with $CH_2Cl_2$. The organic layer was dried over magnesium sulfate, filtered and the solvent evaporated. The residue was purified by column chromatography over silica gel (35-70 μm; eluent: $CH_2Cl_2$/methanol 98:2), yielding 0.051 g of compound 32 (25% yield, melting point: 217° C.).

The methyl alcohol derivative H (0.000252 mol) in THF (3 ml) was added to a mixture of chlorosulfonyl isocyanate (0.000416 mol) in THF (2 ml) at –78° C. The mixture was allowed to warm up to room temperature and then stirred at room temperature for 1 h. Water was added and the mixture was stirred at 70° C. overnight then poured in water and $K_2CO_3$ 10%. The mixture was extracted with $CH_2Cl_2$. The organic layer was dried over magnesium sulfate, filtered and the solvent evaporated. The residue was first crystallized from diethylether, then from acetone, yielding 0.017 g of compound 33 (15% yield, melting point>250° C.).

EXAMPLE 9

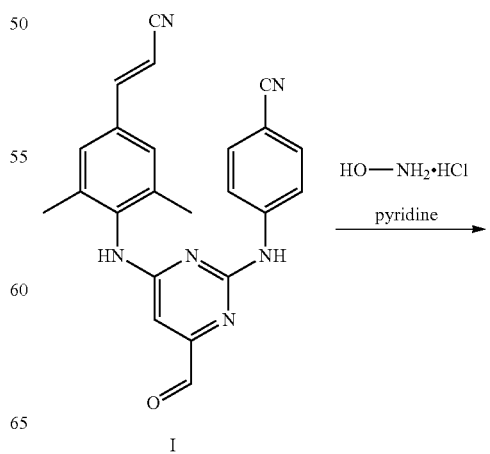

-continued

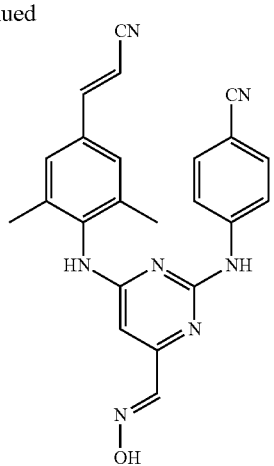

34

A mixture of aldehyde I (0.000330 mol) and hydroxylamine hydrochloride (0.000494 mol) in pyridine (4 ml) was stirred at room temperature for 20 hours, then poured in water. The precipitate was filtered off, washed with water and CH₃CN and dried to give 0.060 g of compound 34 (44% yield, melting point: 220° C.).

Antiviral Spectrum:

Compounds of the invention were tested for their potency against wild type virus and clinically isolated HIV strains harboring one or more mutations associated with resistance to reverse transcriptase inhibitors. Antiviral activity was evaluated using a cellular assay performed according to the following procedure.

The human T-cell line MT4 was engineered with Green Fluorescent Protein (GFP) and a HIV-specific promoter, HIV-1 long terminal repeat (LTR). This cell line, designated MT4 LTR-EGFP, can be used for the in vitro evaluation of anti-HIV activity of investigational compounds. In HIV-1 infected cells, the Tat protein is produced, which upregulates the LTR promotor and eventually leads to stimulation of the GFP reporter production, allowing to measure ongoing HIV-infection fluorometrically.

Analogously, MT4 cells were engineered with GFP and the constitutional cytomegalovirus (CMV) promotor. This cell line was designated MT4 CMV-EGFP and can be used for the in vitro evaluation of cytotoxicity of investigational compounds. In this cell line, GFP levels are comparably to those of infected MT4 LTR-EGFP cells. Cytotoxic investigational compounds reduce GFP levels of mock-infected MT4 CMV-EGFP cells.

Effective concentration values such as 50% effective concentration (EC50) can be determined and are usually expressed in μM. An EC50 value is defined as the concentration of test compound that reduces the fluorescence of HIV-infected cells by 50%. The 50% cytotoxic concentration (CC50 in μM) is defined as the concentration of test compound that reduces fluorescence of the mock-infected cells by 50%. The ratio of CC50 to EC50 is defined as the selectivity index (SI) and is an indication of the selectivity of the anti-HIV activity of the inhibitor. The ultimate monitoring of HIV-1 infection and cytotoxicity was done using a scanning microscope. Image analysis allows very sensitive detection of viral infection. Measurements were done before cell necrosis, which usually takes place about five days after infection, in particular measurements were performed three days after infection.

The columns IIIB, L100I, etc. in the table list the pEC$_{50}$ (-log EC50) values against various strains IIIB, L100I, etc.; pSI lists the -log SI values.

Strain IIIB is wild type HIV strain.

"MDR" refers to a strain that contains mutations L100I, K103N, Y181C, E138G, V179I, L2214F, V278V/I and A327A/V in HIV reverse transcriptase.

| Compound No | IIIB | pSI (IIIB) | L100I + K103N | K103N + Y181C | Y181C | MDR |
|---|---|---|---|---|---|---|
| 1 | 8.46 | 3.26 | 6.94 | 7.71 | 7.96 | 5.75 |
| 2 | 8.44 | 3.56 | 7.12 | 7.15 | 7.74 | 4.95 |
| 3 | 8.14 | >3.54 | 7.02 | 6.58 | 6.98 | 5.53 |
| 4 | 8.51 | 3.63 |  | 7.99 | 7.86 | 5.55 |
| 5 | 8.80 | 3.94 | 7.60 | 8.36 | 8.20 | 5.85 |
| 6 | 8.05 | >3.44 | 7.39 |  | 7.70 | 5.73 |
| 7 | 8.38 | >3.78 |  | 7.75 | 7.78 | 5.63 |
| 8 | 8.26 | >3.66 | 7.07 | 7.50 | 7.73 | 5.09 |
| 10 | 8.55 | 3.62 | 8.32 | 7.97 | 8.46 | 6.25 |
| 11 | 8.74 | 3.63 | 8.20 | 7.72 | 8.39 | 6.16 |
| 12 | 8.62 | 3.51 | 6.50 | 6.78 | 7.28 | 5.57 |
| 13 | 8.54 | 3.50 | 7.20 | 7.68 | 7.79 | 5.59 |
| 14 | 8.52 | 3.22 | 7.00 | 7.76 | 7.85 | 5.67 |
| 15 | 8.54 | 3.59 | 7.42 | 7.86 | 7.89 | 5.55 |
| 16 | 8.54 | 3.60 | 7.06 | 7.61 | 7.60 | 5.64 |
| 17 | 7.80 | 2.70 | 6.41 | 7.04 | 7.01 | 5.56 |
| 18 | 9.05 | 4.05 | 7.48 | 7.79 | 8.06 | 6.33 |
| 19 | 8.48 | 3.50 | 6.83 | 6.97 | 7.68 | 5.32 |
| 20 | 8.46 | 3.36 | 6.33 | 6.96 | 6.99 | 5.30 |
| 21 | 8.47 | 3.44 | 7.16 | 7.71 | 7.73 | 5.70 |
| 22 | 7.93 | 3.25 | 6.35 | 7.02 | 7.09 | 5.50 |
| 23 | 8.80 | 3.78 | 6.98 | 7.78 | 7.72 | 5.67 |
| 24 | 9.16 | 4.09 | 7.31 | 7.84 | 8.14 | 5.75 |
| 25 | 7.63 | 2.02 |  | 7.30 | 7.03 | 5.75 |
| 26 | 8.43 | 3.67 |  | 8.07 | 7.62 | 5.57 |
| 27 | 8.42 | 3.76 |  | 8.51 | 7.79 | 5.93 |
| 28 | 8.68 | 3.67 | 7.27 | 7.82 | 7.81 | 5.68 |
| 29 | 7.70 | 2.47 | 6.66 | 7.01 | 7.06 | 5.67 |
| 30 | 8.55 | 3.74 | 7.56 | 7.89 | 7.69 | 5.80 |
| 31 | 8.41 | 3.60 | 7.13 | 7.71 | 7.48 | 5.48 |
| 32 | 8.50 | >3.90 | 7.20 | 7.50 | 7.60 | 6.40 |
| 33 | 8.40 | 3.70 | 7.10 | 8.00 | 7.70 | 6.20 |
| 34 | 8.40 | 3.40 | 7.90 | 8.40 | 8.00 | 6.30 |

The invention claimed is:
1. A compound of formula

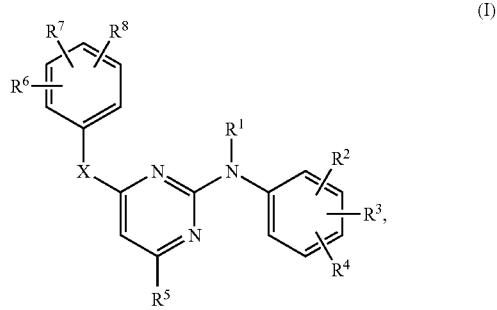

(I)

a pharmaceutically acceptable addition salt, or a stereochemically isomeric form thereof, wherein:

each $R^1$ independently is hydrogen; aryl; formyl; $C_{1-6}$alkylcarbonyl; $C_{1-6}$alkyl; $C_{1-6}$alkyloxycarbonyl;

$R^2$, $R^3$, $R^6$ and $R^7$ independently are hydrogen; hydroxy; halo; $C_{3-7}$cycloalkyl; $C_{1-6}$alkyloxy; carboxyl; $C_{1-6}$alkyloxycarbonyl; cyano; nitro; amino; mono- or di($C_{1-6}$alkyl)amino; polyhalo$C_{1-6}$alkyl; polyhalo$C_{1-6}$alkyloxy; —C(=O)$R^9$; $C_{1-6}$alkyl optionally substituted with halo, cyano or —C(=O)$R^9$; $C_{2-6}$alkenyl optionally substituted with halo, cyano or —C(=O)R⁹; C$_{2-6}$alkynyl optionally substituted with halo, cyano or —C(=O)R⁹;

R⁴ and R⁸ independently are hydroxy; halo; C$_{3-7}$cycloalkyl; C$_{1-6}$alkyloxy; carboxyl; C$_{1-6}$alkyloxycarbonyl; formyl; cyano; nitro; amino; mono- or di(C$_{1-6}$alkyl)amino; polyhaloC$_{1-6}$alkyl; polyhaloC$_{1-6}$alkyloxy; —C(=O)R⁹; —S(=O)$_r$R⁹; —NH—S(=O)$_2$R⁹; —NHC(=O)H; —C(=O)NHNH$_2$; —NHC(=O)R⁹; Het; C$_{1-6}$alkyl optionally substituted with halo, cyano, amino, mono- or di(C$_{1-6}$alkyl)amino, —C(=O)—R⁹, Het or with C$_{1-6}$alkyloxy; C$_{2-6}$alkenyl optionally substituted with halo, cyano, amino, mono- or di(C$_{1-6}$alkyl)amino, —C(=O)—R⁹, Het, or with C$_{1-6}$alkyloxy; C$_{2-6}$alkynyl optionally substituted with halo, cyano, amino, mono- or di(C$_{1-6}$alkyl)amino, —C(=O)—R⁹, Het, or with C$_{1-6}$alkyloxy;

R⁵ is —CH$_2$—O—P(=O)(OR$^{5g}$)$_2$; —CH$_2$—O—C(=O)—NH$_2$; —C(=O)—R$^{5d}$;

each R$^{5d}$ independently is aryl or Het;

each R$^{5g}$ independently is C$_{1-6}$alkyl;

each R⁹ independently is C$_{1-6}$alkyl, amino, mono- or di(C$_{1-6}$alkyl)amino, or polyhalo-C$_{1-6}$alkyl;

X is —NR¹—, —O—, —CH$_2$—, —S—;

each r independently is 1 or 2;

each Het independently is pyridyl, thienyl, furanyl, oxazolyl, isoxazolyl, imidazolyl, pyrazolyl, thiazolyl, thiadiazolyl, oxadiazolyl, quinolinyl, benzothienyl, benzofuranyl; which each may optionally be substituted with one or two substituents each independently selected from C$_{1-6}$alkyl, halo, hydroxy, cyano, C$_{1-6}$alkyloxy, C$_{2-6}$alkenyl substituted with halo, hydroxy or with cyano;

each aryl independently is phenyl or phenyl substituted with one, two, three, four or five substituents each independently selected from halo, hydroxy, mercapto, C$_{1-6}$alkyl, C$_{2-6}$alkenyl, C$_{2-6}$alkynyl, hydroxyC$_{1-6}$alkyl, aminoC$_{1-6}$alkyl, mono or di(C$_{1-6}$alkyl)amino C$_{1-6}$alkyl, C$_{1-6}$alkylcarbonyl, C$_{3-7}$cycloalkyl, C$_{1-6}$alkyloxy, phenylC$_{1-6}$alkyloxy, C$_{1-6}$alkyloxycarbonyl, aminosulfonyl, C$_{1-6}$alkylthio, cyano, nitro, polyhaloC$_{1-6}$alkyl, polyhaloC$_{1-6}$alkyloxy, amino carbonyl, phenyl, and Het.

2. The compound of claim 1 wherein the compound of formula (I) is represented by formula

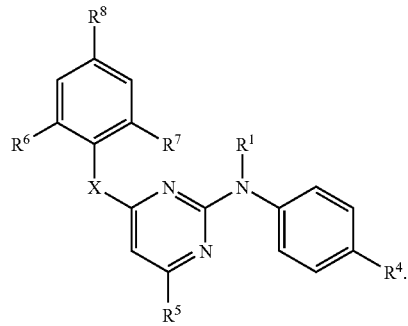

(I-a)

3. The compound of claim 1, wherein R¹ is hydrogen.

4. The compound of claim 1, wherein R², R³, R⁶ and R⁷ independently are hydrogen; halo; C$_{1-6}$alkyl; cyano.

5. The compound of claim 1, wherein R⁴ and R⁸ independently are cyano; C$_{1-6}$alkyl substituted with cyano; C$_{2-6}$alkenyl substituted with cyano.

6. The compound of claim 1, wherein R⁸ is a radical —CH$_2$—CH$_2$—CN, —CH=CH—CN, or —C≡C—CN.

7. The compound of claim 6, wherein R⁸ is a radical —CH=CH—CN.

8. The compound of claim 1, wherein R⁴ is cyano.

9. The compound of claim 1, wherein
R⁵ is
—CH$_2$—O—P(=O)(OR$^{5g}$)$_2$; each R$^{5g}$ is C$_{1-6}$alkyl;
—CH$_2$—O—C(=O)—NH$_2$; or
—C(=O)—R$^{5d}$; wherein R$^{5d}$ is thiazolyl.

10. The compound of claim 1, wherein X is —NH—.

11. The compound of claim 1, wherein each aryl independently is phenyl or phenyl substituted with one, two or three substituents each independently selected from halo, hydroxy, C$_{1-6}$alkyl, C$_{1-6}$alkyloxy, cyano, nitro, trifluoromethyl.

12. A pharmaceutical composition comprising an effective amount of a compound of formula (I) as defined in claim 1 and a carrier.

13. The pharmaceutical composition of claim 12, wherein
R⁵ is
—CH$_2$—O—P(=O)(OR$^{5g}$)$_2$; each R$^{5g}$ is C$_{1-6}$alkyl;
—CH$_2$—O—C(=O)—NH$_2$; or
—C(=O)—R$^{5d}$; wherein R$^{5d}$ is thiazolyl.

14. A pharmaceutical composition comprising an effective amount of a compound of formula (I) as defined in claim 2 and a carrier.

* * * * *